(12) United States Patent
Johnson

(10) Patent No.: US 7,498,136 B2
(45) Date of Patent: Mar. 3, 2009

(54) **METHODS FOR DETECTING MULTIPLE SPECIES AND SUBSPECIES OF *NEISSERIA***

(75) Inventor: Scott C. Johnson, Sun Prairie, WI (US)

(73) Assignee: EraGen Biosciences, Inc., Madison, WI (US)

( * ) Notice: Subject to any disclaimer, the term of this patent is extended or adjusted under 35 U.S.C. 154(b) by 0 days.

(21) Appl. No.: 11/376,952

(22) Filed: Mar. 16, 2006

(65) Prior Publication Data

US 2006/0234266 A1    Oct. 19, 2006

Related U.S. Application Data

(60) Provisional application No. 60/663,542, filed on Mar. 18, 2005.

(51) Int. Cl.
   *C12Q 1/68* (2006.01)
(52) U.S. Cl. ............................................ 435/6
(58) Field of Classification Search .................. None
   See application file for complete search history.

(56) References Cited

U.S. PATENT DOCUMENTS

| | | | |
|---|---|---|---|
| 4,458,066 A | 7/1984 | Caruthers et al. |
| 4,683,195 A | 7/1987 | Mullis et al. |
| 4,683,202 A | 7/1987 | Mullis |
| 4,800,159 A | 1/1989 | Mullis et al. |
| 4,996,143 A | 2/1991 | Heller et al. |
| 5,177,064 A | 1/1993 | Bodor |
| 5,210,015 A | 5/1993 | Gelfand et al. |
| 5,412,088 A | 5/1995 | Jones et al. |
| 5,432,272 A | 7/1995 | Benner |
| 5,470,974 A | 11/1995 | Summerton et al. |
| 5,604,097 A | 2/1997 | Brenner |
| 5,605,794 A | 2/1997 | Rust et al. |
| 5,679,524 A | 10/1997 | Nikiforov et al. |
| 5,681,702 A | 10/1997 | Collins et al. |
| 5,736,330 A | 4/1998 | Fulton |
| 5,843,669 A | 12/1998 | Kaiser et al. |
| 5,846,717 A | 12/1998 | Brow et al. |
| 5,856,092 A | 1/1999 | Dale et al. |
| 5,928,869 A | 7/1999 | Nadeau et al. |
| 5,958,784 A | 9/1999 | Benner |
| 5,965,364 A | 10/1999 | Benner |
| 6,001,983 A | 12/1999 | Benner |
| 6,007,984 A | 12/1999 | Wang et al. |
| 6,037,120 A | 3/2000 | Benner |
| 6,046,807 A | 4/2000 | Chandler |
| 6,054,270 A | 4/2000 | Southern |
| 6,057,107 A | 5/2000 | Fulton |
| 6,140,496 A | 10/2000 | Benner |
| 6,232,462 B1 | 5/2001 | Collins et al. |
| 6,294,336 B1 | 9/2001 | Boyce-Jacino et al. |
| 6,444,798 B1 | 9/2002 | Benner |
| 6,548,250 B1 | 4/2003 | Sorge |
| 6,617,106 B1 | 9/2003 | Benner |
| 6,627,456 B1 | 9/2003 | Benner |
| 6,833,257 B2 | 12/2004 | Lee et al. |
| 6,977,161 B2 | 12/2005 | Grenier et al. |
| 2002/0055104 A1 | 5/2002 | Michelotti |
| 2002/0132221 A1 | 9/2002 | Chee et al. |
| 2002/0150900 A1 | 10/2002 | Marshall et al. |
| 2003/0194705 A1 | 10/2003 | Schroth |
| 2003/0211483 A1* | 11/2003 | Schroeder et al. .............. 435/6 |
| 2004/0106108 A1 | 6/2004 | Grenier et al. |
| 2005/0014163 A1 | 1/2005 | Dong et al. |
| 2006/0078936 A1 | 4/2006 | Grenier et al. |

FOREIGN PATENT DOCUMENTS

| | | |
|---|---|---|
| EP | 0 382 433 B1 | 8/1990 |
| EP | 0 416 817 B1 | 3/1991 |
| EP | 0 742 287 A2 | 11/1996 |
| EP | 0 747 489 A2 | 12/1996 |
| EP | 0 915 174 A1 | 5/1999 |
| WO | WO 90/06042 A2 | 6/1990 |
| WO | WO 94/21820 A1 | 9/1994 |
| WO | WO 96/31622 A1 | 10/1996 |
| WO | WO 97/46711 A1 | 12/1997 |
| WO | WO 98/14610 A2 | 4/1998 |
| WO | WO 98/20157 * | 5/1998 |
| WO | WO 02/070728 * | 9/2002 |
| WO | WO 2004/065550 A2 | 8/2004 |

OTHER PUBLICATIONS

Buck et al.; Design Strategies and Performance of Custom DNA Sequencing Primers, BioTechniques 27:528-536 (Sep. 1999).*
Wang et al., Homogeneous Real-Time Detection of Single-Nucleotide Polymorphisms by Strand Displacement Amplification on the BD ProbeTec ET System, Molecular Diagnostics and Genetics, Clinical Chemistry 49:10, 1599-1607 (2003).*
Johnson et al., A third base pair for the polymerase chain reaction: inserting isoC and isoG, Published online Mar. 29, 2004, Nucleic Acids Research, 2004, vol. 32, No. 6 1937-1941.*
Fiandaca et al., Self-Reporting PNA/DNA Primers for PCR Analysis, Genome Res. 2001 11: 609-613.*

(Continued)

*Primary Examiner*—Kenneth R. Horlick
*Assistant Examiner*—Mark Staples
(74) *Attorney, Agent, or Firm*—Foley & Lardner LLP

(57) ABSTRACT

Disclosed are methods, kits, and other components for detecting multiple nucleic acids in a sample. The methods and kits may be useful for detecting *Neisseria* in a sample. In some embodiments, the methods include (a) reacting a mixture that includes (i) nucleic acid isolated from the sample; (ii) at least a first specific primer capable of being used to amplify specifically nucleic acid of *Neisseria gonorrhea*; (iii) at least a second specific primer capable of being used to amplify specifically nucleic acid of a non-gonococcal species of *Neisseria*; (iv) at least a universal primer capable of being used to amplify specifically nucleic acid of *Neisseria gonorrhea* and nucleic acid of a non-gonococcal species of *Neisseria*; and (b) amplifying and detecting nucleic acid of at least one of *Neisseria gonorrhea* and a non-gonococcal species of *Neisseria*. The disclosed kits may include one or more components for performing the disclosed methods.

16 Claims, No Drawings

OTHER PUBLICATIONS

Macnaughton et al., Accession No. AF146555 entered Jun. 15, 2004.*

Singleton et al., Accession No. AY154623 entered Nov. 10, 2003.*

Biggins et al., "A continuous assay for DNA cleavage: The application of "break lights" to enediynes, iron-dependent agents, and nucleases", *PNAS*, vol. 97, No. 25, Dec. 5, 2000 (pp. 13537-13542).

Cobianchi et al., "Enzymes for Modifying and Labeling DNA and RNA", *Methods in Enzymology*, vol. 152, Copyright © 1987 by Academic Press, Inc., (pp. 94-110).

Hall et al., "Sensitive detection of DNA polymorphisms by the serial invasive signal amplification reaction", *PNAS*, vol. 97, No. 15, Jul. 18, 2000 (pp. 8272-8277).

Horlacher et al., "Recognition by viral and cellular DNA polymerases of nucleosides bearing bases with nonstandard hydrogen bonding patterns", *Proc. Natl. Acad. Sci.*, vol. 92, Jul. 1995 (pp. 6329-6333).

Johnson et al., "A third base pair for the polymerase chain reaction: inserting isoC and isoG", *Nucleic Acids Research*, vol. 32, No. 6, © Oxford University Press 2004 (pp. 1937-1941).

Jurczyk et al., "Synthesis of 2'-Deoxyisoguanosine 5'-Triphosphate and 2'-Deoxy-5-methylisocytidine 5'-Triphosphate", *Helvetica Chimica Acta*, vol. 82, 1999 (pp. 1005-1015).

Lutz, Michael J. et al., "Differential discrimination of DNA polymerases for variants of the non-standard nucleobase pair between xanthosine and 2,4-diaminopyrimidine, two components of an expanded genetic alphabet", *Nucleic Acids Research*, vol. 24, No. 7, 1996 (pp. 1308-1313).

Lutz, Stefan et al., "An in vitro screening technique for DNA polymerases that can incorporate modified nucleotides. Pseudothymidine as a substrate for thermostable polymerases", *Nucleic Acids Research*, vol. 27, No. 13, 1999 (pp. 2792-2798).

Moser et al., "Quantifying Mixed Populations of Drug-Resistant Human Immunodeficiency Virus type 1", *Antimicrobial Agents and Chemotherapy*, vol. 49, No. 8, Aug. 2005 (pp. 3334-3340).

Moser et al., "Enzymatic repair of an expanded genetic information system", *Nucleic Acids Research*, vol. 31, No. 17, 2003 (pp. 5048-5053).

Newton et al., "The production of PCR products with 5' single-stranded tails using primers that incorporate novel phosphoramidite intermediates", *Nucleic Acids Research*, vol. 21, No. 5, 1993 (pp. 1155-1162).

Piccirilli et al., "Enzymatic incorporation of a new base pair into DNA and RNA extends the genetic alphabet", Reprinted from *Nature*, vol. 343, No. 6253, Jan. 4, 1990 (pp. 33-37).

Randerath et al., "$^3$H and $^{32}$P Derivative Methods for Base Composition and Sequence Analysis of RNA", *Methods in Enzymology*, vol. 65, Copyright © 1980 by Academic Press, Inc., (pp. 638-681).

Sepiol et al., "Tautomerism of Isoguanosine and Solvent-Induced Keto-Enol Equilibrium", *Z. Naturforsch*, vol. 31, 1976 (pp. 361-370).

Sismour et al., "The use of thymidine analogs to improve the replication of an extra DNA base pair: a synthetic biological system", *Nucleic Acids Research*, vol. 33, No. 17, 2005 (pp. 5640-5646).

Sismour et al., "PCR amplification of DNA containing non-standard base pairs by variants of reverse transcriptase from Human Immunodeficiency Virus-1", *Nucleic Acids Research*, vol. 32, No. 2, © Oxford University Press 2004 (pp. 728-735).

Switzer et al., "Enzymatic Recognition of the Base Pair between Isocytidine and Isoguanosine", *Biochemistry*, vol. 32, No. 39, 1993 (pp. 10489-10496).

Tabrizi et al., "Evaluation of real time polymerase chain reaction assays for confirmation of *Neisseria gonorrhoeae* in clinical samples tested positive in the Roche Cobas Amplicor assay", *Sex Transm Infect*, vol. 80, 2004 (pp. 68-71).

Tor et al., "Site-Specific Enzymatic Incorporation of an Unnatural Base, $N^6$-(6-Aminohexyl)isoguanosine, into RNA", *J. Am. Chem. Soc.*, vol. 115, No. 11, 1993 (pp. 4461-4467).

Von Krosigk et al., "pH-Independent Triple Helix Formation by an Oligonucleotide Containing a Pyrazine Donor-Donor-Acceptor Base", *J. Am. Chem. Soc.*, vol. 117, No. 19, 1995 (pp. 5361-5362).

Walker et al., "Isothermal in vitro amplification of DNA by a restriction enzyme/DNA polymerase system", *Proc. Natl. Acad. Sci.*, vol. 89, Jan. 1992 (pp. 392-396).

Watanabe et al., "Two-Step Synthesis of 2,5'-Anhydronucleosides From Thymidine, 2'-Deoxyuridine, and 2'-Deoxy-5-fluorouridine", *Nucleic Acid Chemistry*, 1978 (pp. 273-277).

Zubay, "A Case for an Additional RNA Base Pair in Early Evolution", Reprint from: *The Roots of Modern Biochemistry*, © 1988 Walter de Gruyter & Co., Berlin, New York (4 pp.).

Chaudhry et al., "Multiplex polymerase chain reaction assay for the detection of *Neisseria gonorrhoeae* in urogenital specimens", *Current Science*, vol. 83, No. 5, Sep. 10, 2002 (pp. 634-640).

Li et al., "Rapid Identification of Yeasts Commonly Found in Positive Blood Cultures by Amplification of the Internal Transcribed Spacer Regions 1 and 2", *Eur. J. Clin. Microbiol. Infect. Dis.*, vol. 22, 2003 (pp. 693-696).

PCT International Search Report, based on International Application No. PCT/US2006/009376, date of mailing of the International Search Report Nov. 10, 2006 (5 pp.).

Rossau et al., "Nucleotide sequence of a 16S ribosomal RNA gene from *Neisseria gonorrhoeae*", *Nucleic Acids Research*, vol. 18, No. 13, 1988 (p. 6227).

\* cited by examiner

```
                              SEQUENCE LISTING

<160> NUMBER OF SEQ ID NOS: 9

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (1)
<223> OTHER INFORMATION: iC

<400> SEQUENCE: 1
ngtcccaggt accgtcatcg                                                      20

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (1)
<223> OTHER INFORMATION: iC

<400> SEQUENCE: 2
ncaggtcagg taccgtcatc a                                                    21

<210> SEQ ID NO 3
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
gccatgccgc gtgtct                                                          16

<210> SEQ ID NO 4
<211> LENGTH: 77
<212> TYPE: DNA
<213> ORGANISM: Neisseria gonorrhoeae

<400> SEQUENCE: 4
gccatgccgc gtgtctgaag aaggccttcg ggaagaaaag gctgttgcca atatcggcgg          60
ccgatgacgg tacctga                                                         77

<210> SEQ ID NO 5
<211> LENGTH: 77
<212> TYPE: DNA
<213> ORGANISM: Neisseria subflava

<400> SEQUENCE: 5
gccatgccgc gtgtctgaag aaggccttcg ggaagaaaag gctgttgcta atatcgacag          60
```

```
ctgatgacgg tacctga                                                      77

<210> SEQ ID NO 6
<211> LENGTH: 77
<212> TYPE: DNA
<213> ORGANISM: Neisseria perflava

<400> SEQUENCE: 6
gccatgccgc gtgtctgaag aaggccttcg ggaagaaaag gctgttgcta ataccgacag       60
ctgatgacgg tacctga                                                      77

<210> SEQ ID NO 7
<211> LENGTH: 77
<212> TYPE: DNA
<213> ORGANISM: Neisseria cinerea

<400> SEQUENCE: 7
gccatgccgc gtgtctgaag aaggccttcg ggaagaaaag gctgttgcta atatcagcgg       60
ctgatgacgg tacctga                                                      77

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
cactgggact gagacacggc                                                   20

<210> SEQ ID NO 9
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
cgttaatcgg aattactggg cgt                                               23
```

METHODS FOR DETECTING MULTIPLE SPECIES AND SUBSPECIES OF *NEISSERIA*

CROSS-REFERENCE TO RELATED PATENT APPLICATIONS

This application claims the benefit under 35 U.S.C. §119 (e) of U.S. provisional application No. 60/663,542, filed on Mar. 18, 2005, which is incorporated by reference herein in its entirety.

BACKGROUND

The present methods and kits relate broadly to the identification of organisms using nucleic acid amplification techniques. In particular, the methods and kits relate to distinguishing closely related species or subspecies of microorganisms.

In clinical settings, it is often useful to be able to distinguish pathogens from closely related species or subspecies. For example, *Neisseria gonorrhoeae* is recognized as one of the most prevalent sexually transmitted bacteria in the world. Accurate diagnosis of this bacterial infection is critical for preventing serious consequences of long-term infections. Unfortunately, screening efforts in low-prevalence populations coupled with the genomic similarity of many non-gonococcal *Neisseria* species can potentially lead to the generation of false-positive results using amplified detection techniques such as the polymerase chain reaction (PCR). Although the treatment of such infections is relatively safe and inexpensive, the psychosocial implications of false-positive results can be detrimental to the patients involved. Accordingly, new tests for *Neisseria gonorrhoeae* capable of discriminating between *N. gonorrhoeae* and other genomically similar non-gonococcal *Neisseria* species are highly desirable. More generally, there is a need in the art for methods that can distinguish among closely related species or subspecies of microorganisms, especially in a clinical setting.

SUMMARY

There are provided herein methods and kits for quickly, easily and inexpensively distinguishing among closely related species or subspecies of microorganisms. Thus in accordance with one aspect, the present methods and kits provide for the positive identification of multiple species or subspecies of a microorganism including adding two or more specific primers and a universal primer to a sample which comprises nucleic acids from one or more species or subspecies of an organism. The species or subspecies present are either a target species or subspecies and/or one or more non-target species or subspecies. The method further includes amplifying a nucleic acid from each target species or subspecies and non-target species or subspecies present using the one or more specific primers and the universal primer to produce amplification products. The amplification product of the target species or subspecies incorporates a different specific primer from the amplification product of the non-target species. The methods further include detecting the amplification products and distinguishing among the target species or subspecies and the non-target species or subspecies present based on the amplification products that are detected.

Typically, two specific primers are added to the sample, but the methods and kits are not so limited. The specific primers are non-identical in sequence, but can differ by only a single base. The two or more specific primers may comprise a label that is detectable, such as a fluorophore. Suitable fluorophores include, e.g., fluorescein and hexachlorofluorescein. Each specific primer can include a non-natural nucleotide base such as, but not limited to isocytosine or isoguanosine.

Inventive methods can further include adding a non-natural nucleotide base to the sample. Suitable non-natural nucleotide base comprises isoguanosine or isocytosine. Typically the non-natural nucleotide base is complementary to the non-natural nucleotide base used in the specific primers. The non-natural nucleotide base can include a fluorescence quencher such as dabcyl for example.

The amplification of nucleic acids from the target and non-target species or subspecies may be carried out, e.g., with a nucleic acid polymerase using the polymerase chain reaction. Typically the nucleic acids from the target and non-target species is DNA (e.g., genomic or cDNA). In the course of the amplification, the non-natural nucleotide base is incorporated into amplification products that also incorporate the universal primer. The amplification product of the target species hybridizes with the amplification product incorporating the universal primer and the non-natural nucleotide base to produce a detectable change in a signal. Likewise, the amplification product of the non-target species hybridizes with the amplification product incorporating the universal primer and the non-natural nucleotide base to produce a detectable change in a signal. The signal change can be produced by any appropriate method known to those of skill in the art. For example, the signal change may be an increase or decrease in fluorescence. Moreover, the detection of the amplification products can occur during the amplification step (in real-time) or after the amplification step.

Inventive methods may be employed with a wide variety of organisms having multiple species or subspecies including, but not limited to *Neisseria, Streptococcus* B, and vaginosis causing bacteria.

In some embodiments, the methods disclosed herein are used to detect *Neisseria* in a sample. The methods for detecting *Neisseria* in a sample may include: (a) reacting a mixture that includes (i) nucleic acid isolated from the sample; (ii) at least a first specific primer capable of being used to amplify specifically nucleic acid of *Neisseria gonorrhea*; (iii) at least a second specific primer capable of being used to amplify specifically nucleic acid of at least one non-gonococcal species of *Neisseria* (e.g., *Neisseria subflava, Neisseria cinerea*, and *Neisseria perflava*); and (iv) at least a universal primer capable of being used to amplify specifically *Neisseria gonorrhea* and at least one non-gonococcal species of *Neisseria* (e.g., *Neisseria subflava, Neisseria cinerea*, and *Neisseria perflava*); and (b) amplifying and detecting nucleic acid of at least one of *Neisseria gonorrhea* and a non-gonococcal species of *Neisseria* (e.g. *Neisseria subflava, Neisseria cinerea*, and *Neisseria perflava*). In some embodiments, the mixture includes no more than about 5 copies of nucleic acid of *Neisseria gonorrhea* (or no more than about 5 copies of nucleic acid of *Neisseria gonorrhea*).

The specific primers may be designed to have exact complementarity to the target nucleic acid sequence or the specific primers may include mismatches. For example, the specific primers may include at least one non-natural nucleotide that does not base-pair with any corresponding nucleotide in the target nucleic acid sequence. In some embodiments, at least one of the first specific primer and second specific primer include a non-complementary tail at one end of the primer that does not base-pair with the target nucleic acid sequence.

The first specific primer and the second specific primer typically differ in sequence by at least one nucleotide. For example, the first specific primer and second specific primer may differ by a single nucleotide base at the 3' terminal ends of the primers (or within the 5 nucleotides at the 3' terminal end). In some embodiments, the first specific primer and the second specific primer differ by more than one nucleotide.

The first specific primer is capable of being used to specifically amplify a first target nucleic acid that may be present in a sample (e.g., *Neisseria gonorrhea*). The second specific primer is capable of being used to specifically amplify a second target nucleic acid that may be present in a sample (e.g., nucleic acid of at least one non-gonococcal species of *Neisseria* such as *Neisseria cinerea, Neisseria perflava,* and *Neisseria subflava*).

Typically, at least one of the first specific primer and second specific primer comprise a label. In some embodiments, both the first specific primer and second specific primer comprise a label, which may be the same or different. Desirably, both the first specific primer and second specific primer comprise labels which are different. Suitable labels may include fluorophores and quenchers.

In some embodiments, at least one of the first specific primer and second specific primer may comprise a non-natural nucleotide base. In desirably embodiments, both the first specific primer and second specific primer may comprise a non-natural nucleotide base, which may be the same or different. Non-natural nucleotide bases may include nucleotides that do not base pair with A, C, G, T, or U. Non-natural nucleotides may include isoguanosine or isocytosine.

The reaction mixture may include a reporter molecule. For example, the reaction mixture may include a labeled non-natural nucleotide as a reporter molecule. The labeled non-natural nucleotide may be capable of base-pairing with a corresponding non-natural nucleotide present in at least one of the first specific primer and second specific primer. Suitable labels may include fluorophores and quenchers. In desirable embodiments, the non-natural nucleotide is labeled with a quencher that is capable of quenching a fluorophore that is used to label at least one of the first specific primer and the second specific primer (or different fluorophores that are used to label the first specific primer and the second specific primer). The non-natural nucleotide base may include isoguanosine or isocytosine. The non-natural nucleotide base may be present in a reaction mixture and may be incorporated into amplified nucleic acid that includes the universal primer.

Detecting may include observing a change in fluorescence of a label present in at least one of the first specific primer and the second specific primer. In some embodiments, detecting may include observing a change in fluorescence in a label that is present in a reporter present in the reaction mixture. Observing a change in fluorescence may include, but is not limited to observing a decrease in fluorescence, observing an increase in fluorescence, observing fluorescence polarization, and observing fluorescence depolarization.

The primers of the methods may be used to amplify any suitable target nucleic acid. In some embodiments, at least one of the first specific primer, the second specific primer, and the universal primer is capable of specifically amplifying 16S ribosomal nucleic acid (e.g., DNA). For example, at least one of the first specific primer, the second specific primer, and the universal primer may be capable of specifically amplifying 16S ribosomal nucleic acid of at least one of *Neisseria gonorrhea* and a non-gonococcal species of *Neisseria* (e.g. *Neisseria subflava, Neisseria cinerea,* and *Neisseria perflava*). Other suitable targets for *Neisseria* may include the heat shock protein gene (i.e., cpn60).

The method may be suitable for detecting a microorganism of the *Neisseria* genus when the microorganism is present in a mixed population. For example, the mixed population may include other microorganisms of the *Neisseria* genus (e.g., non-gonococcal *Neisseria*). In some embodiments, the methods may be used to detect *Neisseria gonorrhea* when the microorganism represents no more than about 10% of the total population of *Neisseria* in a mixed population. Desirably, the method is useful for detecting *Neisseria gonorrhea* when the microorganism represents no more than about 5% or, even more desirably, no more than 2% of the total population of *Neisseria* in a mixed population. If desired, the representation of *Neisseria gonorrhea* in the total *Neisseria* population may be estimated before, during, or after performing the method by at least one of nucleic acid methods, immunological methods, and microbiological methods. In some embodiments, nucleic acid of *Neisseria gonorrhea* is present in a mixed population of nucleic acid that may include non-gonococcal *Neisseria*. Nucleic acid of *Neisseria gonorrhea* may represent no more than about 10%, 5%, or more desirably 2%, of the total nucleic acid of all *Neisseria* in a sample.

Also disclosed are polynucleotides such as the polynucleotide disclosed in Table 1. For example, in the methods the first specific primer may include SEQ ID NO: 1. The second specific primer may include SEQ ID NO: 2. The universal primer may include SEQ ID NO: 3. Also disclosed are polynucleotides having significant sequence identity to the polynucleotides of SEQ ID NO:1, SEQ ID NO:2, and SEQ ID NO:3. For example, polynucleotides having at least about 95% sequence identity (or 96%, 97%, 98%, or 99% sequence identity) are contemplated, where the polynucleotide having 95% sequence identity (or 96%, 97%, 98%, or 99% sequence identity) can function as a primer for a respective target nucleic acid (e.g., nucleic acid of *Neisseria gonorrhea* or a non-gonococcal *Neisseria* such as *Neisseria subflava, Neisseria cinerea,* and *Neisseria perflava*). Polynucleotides as envisioned herein may include polynucleotides that have a 5 nucleotide sequence at the 3' terminus that differs from a 5 nucleotide sequence at the 3' terminus of any one of SEQ ID NOs:1-3 by single nucleotide (e.g., the 3' terminal nucleotide).

TABLE 1

Neisseria 16S Ribosomal DNA Gene Sequences

Specific Oligonucleotides
5'-FAM-(iC) GTCCCAGGTACC          (SEQ. ID NO: 1)
GTCATCG-3'

5'-HEX-(iC) CAGGTCAGGTAC          (SEQ. ID NO: 2)
CGTCATCA-3'

Universal Oligonucleotide
5'-GCCATGCCGCGTGTCT-3'            (SEQ. ID NO: 3)

*Neisseria gonorrhoeae*
5'-GCCATGCCGCGTGTCTGAAGAAGGCCTTCGG (SEQ. ID NO: 4)
GAAGAAAAGGCTGTTGCCAATATCGGCGGCCGAT
GACGGTACCTGA-3'

*Neisseria subflava*
5'-GCCATGCCGCGTGTCTGAAGAAGGCCTTCGG (SEQ. ID NO: 5)
GAAGAAAAGGCTGTTGCTAATATCGACAGCTGAT
GACGGTACCTGA-3'

*Neisseria perflava*
5'-GCCATGCCGCGTGTCTGAAGAAGGCCTTCGG (SEQ. ID NO: 6)
GAAGAAAAGGCTGTTGCTAATACCGACAGCTGAT
GACGGTACCTGA-3'

*Neisseria cinerea*
5'-GCCATGCCGCGTGTCTGAAGAAGGCCTTCGG (SEQ. ID NO: 7)
GAAGAAAAGGCTGTTGCTAATATCAGCGGCTGAT
GACGGTACCTGA-3'

In some embodiments, the reaction mixture further includes an amplification mixture. The reaction mixture may include one or more of nucleotides (e.g., dATP, dCTP, dGTP, dTTP, UTP), salts, buffers, surfactants, enzymes, and the like. The reaction mixture may include nucleotide analogs such as nucleotides with thio-substituted phosphates (e.g., a thio analog of at least one of dATP, dCTP, dGTP, dTTP, UTP, or non-natural nucleotides such as deoxy isocytosine triphosphate (diCTP) and deoxy iso-guanosine triphosphate (diGTP)) that includes a sulfur atom instead of an oxygen atom in the alpha, beta, or gamma position of the triphosphate). The reaction mixture may include dideoxy analogs of nucleotides (i.e., a 2',3'-dideoxy analog of at least one of ATP, CTP, GTP, TTP, UTP, or non-natural nucleotides such as iCTP and iGTP). The reaction mixture may include phosphoramidite analogs of nucleotides (e.g., a 3' phosphoramidite analog of at least one of dATP, dCTP, dGTP, dTTP, and UTP or non-natural nucleotides such as diCTP and diGTP).

In another aspect of the methods disclosed herein, there are provided kits for identifying multiple species or subspecies of an organism according to the methods disclosed herein. The kits may include: (1) a first specific primer for a nucleic acid of a target species or subspecies of an organism; (2) a second specific primer for a nucleic acid of one or more non-target species or subspecies of the organism; (3) a universal primer; and (4) a non-natural nucleotide base. Typically the first and second specific primers each include a first and second non-natural nucleotide base complementary to the non-natural nucleotide base included in the kit. In some such embodiments, the first specific primer has SEQ ID NO: 1; the second specific primer has SEQ ID NO: 2; the universal primer has SEQ ID NO: 3 and the non-natural nucleotide base comprises deoxyisoguanosine triphosphate. In other such embodiments, the first and second specific primers and the non-natural nucleotide base each independently comprise a label. For example, the labels of the first and second specific primers can be fluorophores and the label of the non-natural nucleotide base can be a fluorescence quencher. Optionally, the kit further comprises other components such as buffers and reagents to perform the methods disclosed herein.

Also disclosed are kits that include at least one component for performing the methods disclosed herein. For example, a kit may include at least one component for detecting *Neisseria* in a sample A kit may include (i) a first specific primer capable of specifically amplifying nucleic acid of *Neisseria gonorrhea*; (ii) a second specific primer capable of specifically amplifying nucleic acid of at least one non-gonococcal species of *Neisseria* (e.g., *Neisseria subflava, Neisseria cinerea*, and *Neisseria perflava*); and (iii) a universal primer capable of specifically amplifying nucleic acid of *Neisseria gonorrhea* and nucleic acid of at least one non-gonococcal species of *Neisseria* (e.g., *Neisseria subflava, Neisseria cinerea*, and *Neisseria perflava*). In some embodiments, at least one of the first specific primer and the second specific may include a non-natural nucleotide base. Typically, at least one of the first specific primer, the second specific primer, and the universal primer comprises a label. For example, both the first specific primer and the second specific primer may include a label which may be the same or different. Suitable labels may include fluorophores and quenchers. The kit also may include a reporter molecule. For example, the kit may include a non-natural nucleotide coupled (e.g., covalently conjugated) to a quencher that is capable of quenching a fluorophore present in at least one of the first specific primer and the second specific primer.

The kits disclosed herein may include primers that are capable of being used to amplify any suitable target sequences. For example, the kits may include a first specific primer, a second specific primer, and a universal primer for which at least one of the first specific primer, the second specific primer, and the universal primer is capable of specifically amplifying 16S ribosomal nucleic acid (e.g., DNA). In some embodiments, at least one of the first specific primer, the second specific primer, and the universal primer is capable of specifically amplifying 16S ribosomal nucleic acid of at least one of *Neisseria gonorrhea* and a non-gonococcal species of *Neisseria* (e.g., *Neisseria subflava, Neisseria cinerea*, and *Neisseria perflava*). Other suitable targets may include the heat shock protein gene (i.e., cpn60).

The kit may include a first primer having the sequence of SEQ ID NO: 1 or having a sequence with substantial identity to SEQ ID NO:1 (e.g., a sequence having 95%, 96%, 97%, 98%, or 99% sequence identity to SEQ ID NO:1). A first primer having substantial identity to SEQ ID NO:1 may be used to amplify a respective target (e.g., *Neisseria gonorrhea*). The kit may include a second primer having the sequence of SEQ ID NO: 2 or having a sequence with substantial identity to SEQ ID NO:2 (e.g., a sequence having 95%, 96%, 97%, 98%, or 99% sequence identity to SEQ ID NO:2). A second primer having substantial identity to SEQ ID NO:2 may be used to amplify a respective target (e.g., a non-gonococcal species of *Neisseria* such as *Neisseria subflava, Neisseria cinerea*, and *Neisseria perflava*). The kit may include a universal primer having the sequence of SEQ ID NO: 3 or having a sequence with substantial identity to SEQ ID NO:3 (e.g., a sequence having 95%, 96%, 97%, 98%, or 99% sequence identity to SEQ ID NO:3). A universal primer having substantial identity to SEQ ID NO:3 may be used to amplify a respective target (e.g., *Neisseria gonorrhea* or a non-gonococcal species of *Neisseria* such as *Neisseria subflava, Neisseria cinerea*, and *Neisseria perflava*).

The kit may include additional components. For example, the kit may include components to provide an amplification mixture.

Also disclosed herein are polynucleotides. For example, polynucleotides as disclosed herein may include a polynucleotide, optionally coupled (e.g., covalently conjugated) to a label, where the polynucleotide has at least about 95% sequence identity (or 96%, 97%, 98%, or 99% sequence identity) to a polynucleotide selected from SEQ ID NOs:1-3. Typically, the polynucleotide is capable of being used as a primer for amplifying nucleic acid of a *Neisseria* microorganism. Polynucleotides as disclosed herein may also include polynucleotides that hybridize under stringent conditions to a polynucleotide selected from SEQ ID NOs:1-3 or to the complement of a polynucleotide selected from SEQ ID NOs: 1-3. Polynucleotides, as disclosed herein, may include a polynucleotide selected from SEQ ID NOs:1-3 in which at least one nucleotide has been replaced with a non-natural nucleotide (e.g., isocytosine and isoguanosine). Polynucleotides, as disclosed herein, may include polynucleotides having a 5 nucleotide sequence at the 3' terminus that differs from a 5 nucleotide sequence of any one of SEQ ID NOs.:1-3 by a single nucleotide (e.g., a single nucleotide at the 3' end), and otherwise the polynucleotide may be at least about 95% identical to any one of SEQ ID NOs:1-3.

The methods and kits can be applied to a wide variety of detection technologies including "real time" or "continuous" detection technologies. In addition, the methods and kits disclosed herein can be incorporated into a variety of mass screening techniques and readout platforms (e.g., microarrays). The methods may be performed in solution. In some embodiments, the methods are performed with a solid substrate to which at least one component of the method or kit is immobilized. For example, the component may be covalently immobilized or non-covalently immobilized to the solid substrate.

DETAILED DESCRIPTION OF THE PREFERRED EMBODIMENTS

Disclosed herein are methods and materials for identifying and distinguishing among closely related species or subspecies of an organism. Specifically, the methods disclosed herein can be used to positively identify a target species or subspecies, non-target species or subspecies or both in a sample.

As used herein, unless otherwise stated, the singular forms "a," "an," and "the" include plural reference. Thus, for example, a reference to "an oligonucleotide" includes a plurality of oligonucleotide molecules, and a reference to "a nucleic acid" is a reference to one or more nucleic acids.

As used herein, the term "sample" is used in its broadest sense. A sample may include a bodily tissue or a bodily fluid including but not limited to blood (or a fraction of blood such as plasma or serum), lymph, mucus, tears, urine, and saliva. A sample may include an extract from a cell, a chromosome, organelle, or a virus. A sample may comprise DNA (e.g., genomic DNA), RNA (e.g., mRNA), and cDNA, any of which may be amplified to provide amplified nucleic acid. A sample may include nucleic acid in solution or bound to a substrate (e.g., as part of a microarray). A sample may comprise material obtained from an environmental locus (e.g., a body of water, soil, and the like) or material obtained from a fomite (i.e., an inanimate object that serves to transfer pathogens from one host to another).

As used herein, the term "microarray" refers to an arrangement of a plurality of polynucleotides, polypeptides, or other chemical compounds on a substrate. The terms "element" and "array element" refer to a polynucleotide, polypeptide, or other chemical compound having a unique and defined position on a microarray.

As used herein, an oligonucleotide is understood to be a molecule that has a sequence of bases on a backbone comprised mainly of identical monomer units at defined intervals. The bases are arranged on the backbone in such a way that they can enter into a bond with a nucleic acid having a sequence of bases that are complementary to the bases of the oligonucleotide. The most common oligonucleotides have a backbone of sugar phosphate units. A distinction may be made between oligodeoxyribonucleotides ("dNTP's"), which do not have a hydroxyl group at the 2' position, and oligoribonucleotides ("NTP's"), which have a hydroxyl group in this position. Oligonucleotides also may include derivatives, in which the hydrogen of the hydroxyl group is replaced with organic groups, e.g., an allyl group.

An oligonucleotide is a nucleic acid that includes at least two nucleotides. Oligonucleotides used in the methods disclosed herein typically include at least about ten (10) nucleotides and more typically at least about fifteen (15) nucleotides. Preferred oligonucleotides for the methods disclosed herein include about 10-25 nucleotides. An oligonucleotide may be designed to function as a "primer." A "primer" is a short nucleic acid, usually a ssDNA oligonucleotide, which may be annealed to a target polynucleotide by complementary base-pairing. The primer may then be extended along the target DNA strand by a DNA polymerase enzyme. Primer pairs can be used for amplification (and identification) of a nucleic acid sequence (e.g., by the polymerase chain reaction (PCR)). An oligonucleotide may be designed to function as a "probe." A "probe" refers to an oligonucleotide, its complements, or fragments thereof, which is used to detect identical, allelic or related nucleic acid sequences. Probes may include oligonucleotides which have been attached to a detectable label or reporter molecule. Typical labels include fluorescent dyes, radioactive isotopes, ligands, chemiluminescent agents, and enzymes.

In some embodiments, oligonucleotides as described herein may include a peptide backbone. For example, the oligonucleotides may include peptide nucleic acids or "PNA." Peptide nucleic acids are described in WO 92/20702, which is incorporated herein by reference.

An oligonucleotide may be designed to be specific for a target nucleic acid sequence in a sample. For example, an oligonucleotide may be designed to include "antisense" nucleic acid sequence of the target nucleic acid. As used herein, the term "antisense" refers to any composition capable of base-pairing with the "sense" (coding) strand of a specific target nucleic acid sequence.

An antisense nucleic acid sequence may be "complementary" to a target nucleic acid sequence. As used herein, the terms "complementary" or "complementarity," when used in reference to nucleic acids (i.e., a sequence of nucleotides such as an oligonucleotide or a target nucleic acid), refer to sequences that are related by base-pairing rules. For natural bases, the base pairing rules are those developed by Watson and Crick. For non-natural bases, as described herein, the base-pairing rules include the formation of hydrogen bonds in a manner similar to the Watson-Crick base pairing rules or by hydrophobic, entropic, or van der Waals forces. As an example, for the sequence "T-G-A", the complementary sequence is "A-C-T." Complementarity can be "partial," in which only some of the bases of the nucleic acids are matched according to the base pairing rules. Alternatively, there can be "complete" or "total" complementarity between the nucleic acids. The degree of complementarity between the nucleic acid strands has effects on the efficiency and strength of hybridization between the nucleic acid strands.

Oligonucleotides as described herein typically are capable of forming hydrogen bonds with oligonucleotides having a complementary base sequence. These bases may include the natural bases such as A, G, C, T and U, as well as artificial bases such as deaza-G. As described herein, a first sequence of an oligonucleotide is described as being 100% complementary with a second sequence of an oligonucleotide when the consecutive bases of the first sequence (read 5'→3') follow the Watson-Crick rule of base pairing as compared to the consecutive bases of the second sequence (read 3'→5'). An oligonucleotide may include nucleotide substitutions. For example, an artificial base may be used in place of a natural base such that the artificial base exhibits a specific interaction that is similar to the natural base.

An oligonucleotide that is specific for a target nucleic acid also may be specific for a nucleic acid sequence that has "homology" to the target nucleic acid sequence. As used herein, "homology" refers to sequence similarity or, interchangeably, sequence identity, between two or more polynucleotide sequences or two or more polypeptide sequences. The terms "percent identity" and "% identity" as applied to polynucleotide sequences, refer to the percentage of residue matches between at least two polynucleotide sequences aligned using a standardized algorithm (e.g., BLAST).

An oligonucleotide that is specific for a target nucleic acid will "hybridize" to the target nucleic acid under suitable conditions. As used herein, "hybridization" or "hybridizing" refers to the process by which a oligonucleotide single strand anneals with a complementary strand through base pairing under defined hybridization conditions. "Specific hybridization" is an indication that two nucleic acid sequences share a high degree of complementarity. Specific hybridization complexes form under permissive annealing conditions and remain hybridized after any subsequent washing steps. Permissive conditions for annealing of nucleic acid sequences are routinely determinable by one of ordinary skill in the art and may occur, for example, at 65° C. in the presence of about 6×SSC. Stringency of hybridization may be expressed, in part, with reference to the temperature under which the wash steps are carried out. Such temperatures are typically selected to be about 5° C. to 20° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Equations for calculating $T_m$ and conditions for nucleic acid hybridization are known in the art. Oligonucleotides used as specific primers for amplifying a target nucleic acid generally are capable of specifically hybridizing to the target nucleic acid.

As used herein, "nucleic acid," "nucleotide sequence," or "nucleic acid sequence" refer to a nucleotide, oligonucleotide, polynucleotide, or any fragment thereof and to naturally occurring or synthetic molecules. These phrases also refer to DNA or RNA of genomic or synthetic origin which may be single-stranded or double-stranded and may represent the sense or the antisense strand, or to any DNA-like or RNA-like material. An "RNA equivalent," in reference to a DNA sequence, is composed of the same linear sequence of nucleotides as the reference DNA sequence with the exception that all occurrences of the nitrogenous base thymine are replaced with uracil, and the sugar backbone is composed of ribose instead of deoxyribose. RNA may be used in the methods described herein and/or may be converted to cDNA by reverse-transcription for use in the methods described herein.

As used herein, "amplification" or "amplifying" refers to the production of additional copies of a nucleic acid sequence. Amplification is generally carried out using polymerase chain reaction (PCR) technologies known in the art. The term "amplification reaction system" refers to any in vitro means for multiplying the copies of a target sequence of nucleic acid. The term "amplification reaction mixture" refers to an aqueous solution comprising the various reagents used to amplify a target nucleic acid. These may include enzymes (e.g., a thermostable polymerase), aqueous buffers, salts, amplification primers, target nucleic acid, and nucleoside triphosphates, and optionally at least one labeled probe and/or optionally at least one agent for determining the melting temperature of an amplified target nucleic acid (e.g., a fluorescent intercalating agent that exhibits a change in fluorescence in the presence of double-stranded nucleic acid).

The amplification methods described herein my include "real-time monitoring" or "continuous monitoring." These terms refer to monitoring multiple times during a cycle of PCR, preferably during temperature transitions, and more preferably obtaining at least one data point in each temperature transition. The term "homogeneous detection assay" is used to describe an assay that includes coupled amplification and detection, which may include "real-time monitoring" or "continuous monitoring."

Amplification of nucleic acids may include amplification of nucleic acids or subregions of these nucleic acids. For example, amplification may include amplifying portions of nucleic acids between 50 and 300 bases long by selecting the proper primer sequences and using the PCR.

The disclosed methods may include amplifying at least one nucleic acid in the sample (preferably two nucleic acid, an more preferably three nucleic acids). In the disclosed methods, amplification may be monitored using real-time methods. Amplification mixtures may include natural nucleotides (e.g., nucleotides having A, C, G, T, and U as a nucleobase) and non-natural nucleotides (i.e., nucleotides having other than A, C, G, T, and U as a nucleobase, e.g., nucleotides that include iC and iG as a nucleobase). Non-natural nucleotides and bases are described in U.S. patent application publication 2002-0150900, which is incorporated herein by reference in its entirety. The nucleotides, which may include non-natural nucleotides may include a label (e.g., a quencher or a fluorophore).

The oligonucleotides of the present methods may function as primers. In some embodiments, the oligonucleotides are labeled. For example, the oligonucleotides may be labeled with a reporter that emits a detectable signal (e.g., a fluorophore). The oligonucleotides may include at least one non-natural nucleotide. For example, the oligonucleotides may include at least one nucleotide that includes a nucleobase other than A, C, G, T, or U (e.g., iC or iG). Where the oligonucleotide is used as a primer for PCT, the amplification mixture may include at least one nucleotide that is labeled with a quencher (e.g., Dabcyl). The labeled nucleotide may include at least one non-natural nucleotide. For example, the labeled nucleotide may include at least one nucleobase that is not A, C, G, T, or U (e.g., iC or iG).

In some embodiments, the oligonucleotide may be designed not to form an intramolecular structure such as a hairpin. In other embodiments, the oligonucleotide may be designed to form an intramolecular structure such as a hairpin. For example, the oligonucleotide may be designed to form a hairpin structure that is altered after the oligonucleotide hybridizes to a target nucleic acid, and optionally, after the target nucleic acid is amplified using the oligonucleotide as a primer.

The oligonucleotide may be labeled with a fluorophore that exhibits quenching when incorporated in an amplified product as a primer. In other embodiments, the oligonucleotide may emit a detectable signal after the oligonucleotide is incorporated in an amplified product as a primer (e.g., inherently, or by fluorescence induction or fluorescence dequenching). Such primers are known in the art (e.g., LightCycler primers, Amplifluor® Primers, Scorpion® Primers and Lux™ Primers). The fluorophore used to label the oligonucleotide may emit a signal when intercalated in double-stranded nucleic acid. As such, the fluorophore may emit a signal after the oligonucleotide is used as a primer for amplifying the nucleic acid.

The oligonucleotides that are used in the disclosed methods may be suitable as primers for amplifying at least one nucleic acid in the sample and as probes for detecting at least one nucleic acid in the sample. In some embodiments, the oligonucleotides are labeled with at least one fluorescent dye, which may produce a detectable signal. The fluorescent dye may function as a fluorescence donor for fluorescence resonance energy transfer (FRET). The detectable signal may be quenched when the oligonucleotide is used to amplify a target nucleic acid. For example, the amplification mixture may include nucleotides that are labeled with a quencher for the detectable signal emitted by the fluorophore. Optionally, the oligonucleotides may be labeled with a second fluorescent dye or a quencher dye that may function as a fluorescence acceptor (e.g., for FRET). Where the oligonucleotide is labeled with a first fluorescent dye and a second fluorescent dye, a signal may be detected from the first fluorescent dye, the second fluorescent dye, or both.

The disclosed methods may be performed with any suitable number of oligonucleotides. Where a plurality of oligonucleotides are used (e.g., two or more oligonucleotides), different oligonucleotide may be labeled with different fluorescent dyes capable of producing a detectable signal. In some embodiments, oligonucleotides are labeled with at least one of two different fluorescent dyes. In further embodiments, oligonucleotides are labeled with at least one of three different fluorescent dyes.

In some embodiments, each different fluorescent dye emits a signal that can be distinguished from a signal emitted by any other of the different fluorescent dyes that are used to label the oligonucleotides. For example, the different fluorescent dyes may have wavelength emission maximums all of which differ from each other by at least about 5 nm (preferably by least about 10 nm). In some embodiments, each different fluorescent dye is excited by different wavelength energies. For example, the different fluorescent dyes may have wavelength absorption maximums all of which differ from each other by at least about 5 nm (preferably by at least about 10 nm).

Where a fluorescent dye is used to determine the melting temperature of a nucleic acid in the method, the fluorescent dye may emit a signal that can be distinguished from a signal emitted by any other of the different fluorescent dyes that are used to label the oligonucleotides. For example, the fluorescent dye for determining the melting temperature of a nucleic acid may have a wavelength emission maximum that differs from the wavelength emission maximum of any other fluorescent dye that is used for labeling an oligonucleotide by at least about 5 nm (preferably by least about 10 nm). In some embodiments, the fluorescent dye for determining the melting temperature of a nucleic acid may be excited by different wavelength energy than any other of the different fluorescent dyes that are used to label the oligonucleotides. For example, the fluorescent dye for determining the melting temperature of a nucleic acid may have a wavelength absorption maximum that differs from the wavelength absorption maximum of any fluorescent dye that is used for labeling an oligonucleotide by at least about 5 nm (preferably by least about 10 nm).

The methods may include determining the melting temperature of at least one nucleic acid in a sample (e.g., "amplified nucleic acid" otherwise called "an amplicon"), which may be used to identify the nucleic acid. Determining the melting temperature may include exposing an amplicon to a temperature gradient and observing a detectable signal from a fluorophore. Optionally, where the oligonucleotides of the method are labeled with a first fluorescent dye, determining the melting temperature of the detected nucleic acid may include observing a signal from a second fluorescent dye that is different from the first fluorescent dye. In some embodiments, the second fluorescent dye for determining the melting temperature of the detected nucleic acid is an intercalating agent. Suitable intercalating agents may include, but are not limited to SYBR™ Green 1 dye, SYBR dyes, PICO GREEN® dye, SYTO dyes, SYTOX dyes, ethidium bromide, ethidium homodimer-1, ethidium homodimer-2, ethidium derivatives, acridine, acridine orange, acridine derivatives, ethidium-acridine heterodimer, ethidium monoazide, propidium iodide, cyanine monomers, 7-aminoactinomycin D, YOYO- 1, TOTO-1, YOYO-3, TOTO-3, POPO-1, BOBO-1, POPO-3, BOBO-3, LOLO-1, JOJO-1, cyanine dimers, YO-PRO-1, TO-PRO-1, YO-PRO-3, TO-PRO-3, TO-PRO-5, PO-PRO-1, BO-PRO-1, PO-PRO-3, BO-PRO-3, LO-PRO-1, JO-PRO-1, and mixture thereof. In suitable embodiments, the selected intercalating agent is SYBR™ Green 1 dye.

Typically, an intercalating agent used in the method will exhibit a change in fluorescence when intercalated in double-stranded nucleic acid. A change in fluorescence may include an increase in fluorescence intensity or a decrease in fluorescence intensity. For example, the intercalating agent may exhibit a increase in fluorescence when intercalated in double-stranded nucleic acid, and a decrease in fluorescence when the double-stranded nucleic acid is melted. A change in fluorescence may include a shift in fluorescence spectra (i.e., a shift to the left or a shift to the right in maximum absorbance wavelength or maximum emission wavelength). For example, the intercalating agent may emit a fluorescent signal of a first wavelength (e.g., green) when intercalated in double-stranded nucleic and emit a fluorescent signal of a second wavelength (e.g., red) when not intercalated in double-stranded nucleic acid. A change in fluorescence of an intercalating agent may be monitored at a gradient of temperatures to determine the melting temperature of the nucleic acid (where the intercalating agent exhibits a change in fluorescence when the nucleic acid melts).

In the disclosed methods, each of these amplified target nucleic acids may have different melting temperatures. For example, each of these amplified target nucleic acids may have a melting temperature that differs by at least about 1° C., more preferably by at least about 2° C., or even more preferably by at least about 4° C. from the melting temperature of any of the other amplified target nucleic acids.

The methods disclosed herein may include transcription of RNA to DNA (i.e., reverse transcription). For example, reverse transcription may be performed prior to amplification.

As used herein, "labels" or "reporter molecules" are chemical or biochemical moieties useful for labeling a nucleic acid (including a single nucleotide), amino acid, or antibody. "Labels" and "reporter molecules" include fluorescent agents, chemiluminescent agents, chromogenic agents, quenching agents, radionuclides, enzymes, substrates, cofactors, inhibitors, magnetic particles, and other moieties known in the art. "Labels" or "reporter molecules" are capable of generating a measurable signal and may be covalently or noncovalently joined to an oligonucleotide or nucleotide (e.g., a non-natural nucleotide).

The oligonucleotides and nucleotides (e.g., non-natural nucleotides) of the disclosed methods may be labeled with a "fluorescent dye" or a "fluorophore." As used herein, a "fluorescent dye" or a "fluorophore" is a chemical group that can be excited by light to emit fluorescence. Some suitable fluorophores may be excited by light to emit phosphorescence. Dyes may include acceptor dyes that are capable of quenching a fluorescent signal from a fluorescent donor dye. Dyes that may be used in the disclosed methods include, but are not limited to, the following dyes and/or dyes sold under the following tradenames: 1,5 IAEDANS; 1,8-ANS; 4-Methylumbelliferone; 5-carboxy-2,7-dichlorofluorescein; 5-Carboxyfluorescein (5-FAM); 5-Carboxytetramethylrhodamine (5-TAMRA); 5-FAM (5-Carboxyfluorescein); 5-HAT (Hydroxy Tryptamine); 5-Hydroxy Tryptamine (HAT); 5-ROX (carboxy-X-rhodamine); 5-TAMRA (5-Carboxytetramethylrhodamine); 6-Carboxyrhodamine 6G; 6-CR 6G; 6-JOE; 7-Amino-4-methylcoumarin; 7-Aminoactinomycin D (7-AAD); 7-Hydroxy-4-methylcoumarin; 9-Amino-6-chloro-2-methoxyacridine; ABQ; Acid Fuchsin; ACMA (9-Amino-6-chloro-2-methoxyacridine); Acridine Orange; Acridine Red; Acridine Yellow; Acriflavin; Acriflavin Feulgen SITSA; ALEXA FLUOR 350™ dye; ALEXA FLUOR 430™ dye; ALEXA FLUOR 488™ dye; ALEXA FLUOR 532™ dye; ALEXA FLUOR 546™ dye; ALEXA FLUOR 568™ dye; ALEXA FLUOR 594™ dye; ALEXA FLUOR 633™ dye; ALEXA FLUOR 647™ dye; ALEXA FLUOR 660™ dye; ALEXA FLUOR 680™ dye; Alizarin Complexon; Alizarin Red; Allophycocyanin (APC); AMC; AMCA-S; AMCA (Aminomethylcoumarin); AMCA-X; Aminoactinomycin D; Aminocoumarin; Aminomethylcoumarin (AMCA); Anilin Blue; Anthrocyl stearate; APC (Allophycocyanin); APC-Cy7; APTS; Astrazon Brilliant Red 4G; Astrazon Orange R; Astrazon Red 6B; Astrazon Yellow 7 GLL; Atabrine; ATTO-TAG™ CBQCA dye; ATTO-TAG™ FQ dye; Auramine; Aurophosphine G; Aurophosphine; BAO 9 (Bisaminophenyloxadiazole); Berberine Sulphate; Beta Lactamase; BFP blue shifted GFP (Y66H); Blue Fluorescent Protein; BFP/GFP FRET; Bimane; Bisbenzamide; Bisbenzimide (Hoechst); Blancophor FFG; Blancophor SV; BOBO™-1 dye; BOBO™-3 dye; BODIPY 492/515 dye; BODIPY 493/503 dye; BODIPY 500/510 dye; BODIPY 505/515 dye; BODIPY 530/550 dye; BODIPY 542/563 dye; BODIPY 558/568 dye; BODIPY 564/570 dye; BODIPY 576/589 dye; BODIPY 581/591 dye; BODIPY 630/650-X dye; BODIPY 650/665-X dye; BODIPY 665/676 dye; BODIPY FL dye; BODIPY FL ATP dye; BODIPY Fl-Ceramide dye; BODIPY R6G SE dye; BODIPY TMR dye; BODIPY TMR-X conjugate dye; BODIPY TMR-X, SE dye; BODIPY TR dye; BODIPY TR ATP dye; BODIPY TR-X SE dye; BO-PRO™-1 dye; BO-PRO™-3 dye; Brilliant Sulphoflavin FF; Calcein; Calcein Blue; CALCIUM CRIMSON™ dye; Calcium Green; Calcium Orange; Calcofluor White; Carboxy-X-rhodamine (5-ROX); CASCADE BLUE™ dye; Cascade Yellow; Catecholamine; CCF2 (GeneBlazer); CFDA; CFP-Cyan Fluorescent Protein; CFP/YFP FRET; Chlorophyll; Chromomycin A; CL-NERF (Ratio Dye, pH); CMFDA; Coelenterazine f; Coelenterazine fcp; Coelenterazine h; Coelenterazine hcp; Coelenterazine ip; Coelenterazine n; Coelenterazine O; Coumarin Phalloidin; C-phycocyanine; CPM Methylcoumarin; CTC; CTC Formazan; CY2™ dye; CY3.1 8; CY3.5™ dye; CY3™ dye; CY5.1 8; CY5.5™ dye; CY5™ dye; CY7™ dye; Cyan GFP; cyclic AMP Fluorosensor (FiCRhR); Dabcyl; Dansyl; Dansyl Amine; Dansyl Cadaverine; Dansyl Chloride; Dansyl DHPE; Dansyl fluoride; DAPI; Dapoxyl; Dapoxyl 2; Dapoxyl 3; DCFDA; DCFH (Dichlorodihydrofluorescein Diacetate); DDAO; DHR (Dihydrorhodamine 123); Di-4-ANEPPS; Di-8-ANEPPS (non-ratio); DiA (4-Di-16-ASP); Dichlorodihydrofluorescein Diacetate (DCFH); DiD-Lipophilic Tracer; DiD (DiIC18(5)); DIDS; Dihydrorhodamine 123 (DHR); DiI (DiIC18(3)); Dinitrophenol; DiO (DiOC18(3)); DiR; DiR (DiIC18(7)); DNP; Dopamine; DsRed; DTAF; DY-630-NHS; DY-635-NHS; EBFP; ECFP; EGFP; ELF 97; Eosin; Erythrosin; Erythrosin ITC; Ethidium Bromide; Ethidium homodimer-1 (EthD-1); Euchrysin; EukoLight; Europium (III) chloride; EYFP; Fast Blue; FDA; Feulgen (Pararosaniline); FITC; Flazo Orange; Fluo-3; Fluo-4; Fluorescein (FITC); Fluorescein Diacetate; Fluoro-Emerald; Fluoro-Gold (Hydroxystilbamidine); Fluor-Ruby; FluorX; FM 1-43™ dye; FM 4-46; FURA RED™ dye; FURA RED™/Fluo-3 dye; Fura-2; Fura-2/BCECF; Genacryl Brilliant Red B; Genacryl Brilliant Yellow 10GF; Genacryl Pink 3G; Genacryl Yellow 5GF; GeneBlazer (CCF2); GFP (S65T); GFP red shifted (rsGFP); GFP wild type, non-UV excitation (wtGFP); GFP wild type, UV excitation (wtGFP); GFPuv; Gloxalic Acid; Granular Blue; Haematoporphyrin; Hoechst 33258; Hoechst 33342; Hoechst 34580; HPTS; Hydroxycoumarin; Hydroxystilbamidine (FluoroGold); Hydroxytryptamine; Indo-1; Indodicarbocyanine (DiD); Indotricarbocyanine (DiR); Intrawhite Cf; JC-1; JO-JO-1; JO-PRO-1; Laurodan; LDS 751(DNA); LDS 751 (RNA); Leucophor PAF; Leucophor SF; Leucophor WS; Lissamine Rhodamine; Lissamine Rhodamine B; Calcein/Ethidium homodimer; LOLO-1; LO-PRO-1; Lucifer Yellow; Lyso Tracker Blue; Lyso Tracker Blue-White; Lyso Tracker Green; Lyso Tracker Red; Lyso Tracker Yellow; LysoSensor Blue; LysoSensor Green; LysoSensor Yellow/Blue; Mag Green; Magdala Red (Phloxin B); Mag-Fura Red; Mag-Fura-2; Mag-Fura-5; Mag-Indo-1; Magnesium Green; Magnesium Orange; Malachite Green; Marina Blue; Maxilon Brilliant Flavin 10 GFF; Maxilon Brilliant Flavin 8 GFF; Merocyanin; Methoxycoumarin; Mitotracker Green FM; Mitotracker Orange; Mitotracker Red; Mitramycin; Monobromobimane; Monobromobimane (mBBr-GSH); Monochlorobimane; MPS (Methyl Green Pyronine Stilbene); NBD; NBD Amine; Nile Red; NED™; Nitrobenzoxadidole; Noradrenaline; Nuclear Fast Red; Nuclear Yellow; Nylosan Brilliant Iavin E8G; Oregon Green; Oregon Green 488-X; OREGON GREEN™ dye; OREGON GREEN™ 488 dye; OREGON GREEN™ 500 dye; OREGON GREEN™ 514 dye; Pacific Blue; Pararosaniline (Feulgen); PBFI; PE-Cy5; PE-Cy7; PerCP; PerCP-Cy5.5; PE-TexasRed [Red 613]; Phloxin B (Magdala Red); Phorwite AR; Phorwite BKL; Phorwite Rev; Phorwite RPA; Phosphine 3R; Phycoerythrin B [PE]; Phycoerythrin R [PE]; PKH26 (Sigma); PKH67; PMIA; Pontochrome Blue Black; POPO-1; POPO-3; PO-PRO-1; PO-PRO-3; Primuline; Procion Yellow; Propidium Iodid (PI); PyMPO; Pyrene; Pyronine; Pyronine B; Pyrozal Brilliant Flavin 7GF; QSY 7; Quinacrine Mustard; Red 613 [PE-TexasRed]; Resorufin; RH 414; Rhod-2; Rhodamine; Rhodamine 110; Rhodamine 123; Rhodamine 5 GLD; Rhodamine 6G; Rhodamine B; Rhodamine B 200; Rhodamine B extra; Rhodamine BB; Rhodamine BG; Rhodamine Green; Rhodamine Phallicidine; Rhodamine Phalloidine; Rhodamine Red; Rhodamine WT; Rose Bengal; R-phycocyanine; R-phycoerythrin (PE); RsGFP; S65A; S65C; S65L; S65T; Sapphire GFP; SBFI; Serotonin; Sevron Brilliant Red 2B; Sevron Brilliant Red 4G; Sevron Brilliant Red B; Sevron Orange; Sevron Yellow L; sgBFP™; sgBFP™ (super glow BFP); sgGFP™ dye; sgGFP™ dye (super glow GFP); SITS; SITS (Primuline); SITS (Stilbene Isothiosulphonic Acid); SNAFL calcein; SNAFL-1; SNAFL-2; SNARF calcein; SNARF1; Sodium Green; SpectrumAqua; SpectrumGreen; SpectrumOrange; Spectrum Red; SPQ (6-methoxy-N-(3-sulfopropyl)quinolinium); Stilbene; Suiphorhodamine B can C; Suiphorhodamine G Extra; SYTO 11; SYTO 12; SYTO 13; SYTO 14; SYTO 15; SYTO 16; SYTO 17; SYTO 18; SYTO 20; SYTO 21; SYTO 22; SYTO 23; SYTO 24; SYTO 25; SYTO 40; SYTO 41; SYTO 42; SYTO 43; SYTO 44; SYTO 45; SYTO 59; SYTO 60; SYTO 61; SYTO 62; SYTO 63; SYTO 64; SYTO 80; SYTO 81; SYTO 82; SYTO 83; SYTO 84; SYTO 85; SYTOX Blue; SYTOX Green; SYTOX Orange; TET™ dye; Tetracycline; Tetramethylrhodamine (TRITC); TEXAS RED™ dye; Texas Red-X™ conjugate; Thiadicarbocyanine (DiSC3); Thiazine Red R; Thiazole Orange; Thioflavin 5; Thioflavin S; Thioflavin TCN; Thiolyte; Thiozole Orange; Tinopol CBS (Calcofluor White); TMR; TO-PRO-1; TO-PRO-3; TO-PRO-5; TOTO-1; TOTO -3; TriColor (PE-Cy5); TRITC TetramethylRodamineIsoThioCyanate; True Blue; TruRed; Ultralite; Uranine B; Uvitex SFC; VIC® dye; wt GFP; WW 781; X-Rhodamine; XRITC; Xylene Orange; Y66F; Y66H; Y66W; Yellow GFP; YFP; YO-PRO-1; YO-PRO-3; YOYO-1; YOYO-3; and salts thereof.

Fluorescent dyes or fluorophores may include derivatives that have been modified to facilitate conjugation to another reactive molecule. As such, fluorescent dyes or fluorophores may include amine-reactive derivatives such as isothiocyanate derivatives and/or succinimidyl ester derivatives of the fluorophore.

The oligonucleotides and nucleotides of the disclosed methods (e.g., non-natural nucleotides) may be labeled with a quencher. Quenching may include dynamic quenching (e.g., by FRET), static quenching, or both. Suitable quenchers may include Dabcyl. Suitable quenchers may also include dark quenchers, which may include black hole quenchers sold under the tradename "BHQ" (e.g., BHQ-0, BHQ-1, BHQ-2, and BHQ-3, Biosearch Technologies, Novato, Calif.). Dark quenchers also may include quenchers sold under the tradename "QXL™" (Anaspec, San Jose, Calif.). Dark quenchers also may include DNP-type non-fluorophores that include a 2,4-dinitrophenyl group.

The oligonucleotides or nucleotides (e.g., non-natural nucleotides) of the present methods may be labeled with a donor fluorophore and an acceptor fluorophore (or quencher dye) that are present in the oligonucleotides at positions that are suitable to permit FRET (or quenching). Labeled oligonucleotides that are suitable for the present methods may include but are not limited to oligonucleotides designed to function as LightCycler primers or probes, Taqman® Probes, Molecular Beacon Probes, Amplifluor® Primers, Scorpion® Primers, and LUX™ Primers.

In some embodiments, the disclosed assays are used for the detection of nucleic acid associated with *Neisseria* species or subspecies. For example, the assays may utilize MultiCode®-RTx PCR technology, which is disclosed in U.S. Patent Application Publication No. 2002-0150900, incorporated herein by reference. The assays may be performed using real-time or continuous methods using any suitable commercial thermal cycler. The disclosed technology may be used to detect nucleic acid targets obtained from any source (e.g., human, animal and infectious disease samples). Advantages of the MultiCode®-RTx system may include: high sensitivity, high specificity, rapid cycling with real-time readout, thermal melt at the end of run to verify specific amplification of target sequences, inclusion of internal RT-PCR control, excellent stability, and rapid creation of new assays based on genetic sequences.

The methods disclosed herein may use PCR to amplify nucleic acids from the target and/or non-target species. The PCR can be a Fast-shot™ amplification. The methods disclosed herein may utilize two or more specific primers, a universal primer, and, typically a non-natural nucleotide base and nucleic acid polymerase. Other assay methods using non-natural nucleotide bases are described in U.S. patent application Ser. No. 10/861,292, filed May 18, 2001.

As used herein, "target species" or "target subspecies" refers to a species or subspecies of an organism, in or suspected to be in a sample. The target species or subspecies contains a target nucleic acid that may be used to distinguish it from non-target species or subspecies.

As used herein, "non-target species" or "non-target subspecies" refers to one or more species or subspecies of an organism different from the target species or subspecies. A non-target species or subspecies is distinguished from the target species or subspecies by containing a nucleic acid that is similar but not identical to the target nucleic acid of the target species or subspecies.

As used herein, "target nucleic acid" refers to a nucleic acid containing a nucleic acid sequence, suspected to be in a sample and to be detected or quantified in a method or system as disclosed herein. Target nucleic acids contain the target nucleic acid sequences that are actually assayed during an assay procedure. The target can be directly or indirectly assayed. In at least some embodiments, the target nucleic acid, if present in the sample, is used as a template for amplification according to the methods disclosed herein.

As used herein, the term "thermostable nucleic acid polymerase" refers to an enzyme that catalyzes the polymerization of nucleosides and which is relatively stable to heat when compared, for example, to nucleotide polymerases from *E. coli*. Generally, the enzyme will initiate synthesis at the 3'-end of the primer annealed to the target sequence, and will proceed in the 5'-direction along the template, and if possessing a 5' to 3' nuclease activity, hydrolyzing an intervening, annealed oligonucleotide to release intervening nucleotide bases or oligonucleotide fragments, until synthesis terminates. A thermostable enzyme has activity at a temperature of at least about 37° C. to about 42° C., typically in the range from about 50° C. to about 75° C. Representative thermostable polymerases include, for example, thermostable polymerases such as native and altered polymerases of *Thermus* species, including, but not limited to, *Thermus aquaticus* (Taq), *Thermus flavus* (Tfl), and *Thermus thermophilus* (Tth), and of the *Thermotoga* species, including, but not limited to, *Thermotoga neapolitana*.

As used herein, the term "DNA mutant" or "DNA polymorphism" refers to the condition in which two or more different nucleotide sequences can exist at a particular site in DNA and includes any nucleotide variation, such as single or multiple nucleotide substitutions, deletions or insertions. These nucleotide variations can be species specific, mutant or polymorphic variations (e.g., allele specific variations). At least some of the embodiments of the methods described herein can detect single nucleotide changes in nucleic acids such as occur in β-globin genetic diseases caused by single-base mutations, additions or deletions (some β-thalassemias, sickle cell anemia, hemoglobin C disease, etc.), as well as multiple-base variations such as ar involved with α-thalassemia or some β-thalassemias. In addition, the process herein can detect polymorphisms, which are not necessarily associated with a disease, but are merely a condition in which two or more different nucleotide sequences (whether having substituted, deleted or inserted nucleotide base pairs) can exist at a particular site in the nucleic acid in the population, as with HLA regions of the human genome and random polymorphisms such as mitochondrial DNA.

As used herein, a "specific primer" means an oligonucleotide that can specifically hybridize to a target nucleic acid and that is suitable as a primer for amplification of the target nucleic acid. For example, a "specific primer" may specifically hybridize to a target nucleic acid because the specific primer is complementary to the target nucleic acid. "Complementarity" may include full or complete complementarity. However, a primer may be specific for a target nucleic acid without being fully or completely complementary. A primer may specifically hybridize to a target acid under suitable conditions (e.g., under conditions which A-T and G-C base pairing occurs). A primer may specifically hybridize to a target acid under suitable conditions that include high stringent conditions.

As used herein, "universal primer" refers to a primer that can specifically hybridize to two or more different target nucleic acids in a sample (e.g., 3 or more, 4 or more, 5 or more, 10 or more, 15 or more, or 25 or more different target nucleic acids in a sample). A "universal primer" may hybridize to a region of the different target nucleic acids that is identical or that has substantial identity to provide for specific hybridization of the "universal primer" to the different target nucleic acids. A "universal primer" may be complementary to a nucleic acid sequence that is common to all the species or subspecies of the organism being identified by the methods disclosed herein. Thus for example, SEQ ID NO: 3 (see Table 1) is a universal primer for *N. gonnorhoeae, N. subflava, N. perflava*, and *N. cinerea*.

In some embodiments of the methods and kits disclosed herein, a sample is suspected to contain a target species or subspecies, and hence a target nucleic acid (e.g., a cDNA). The target nucleic acid typically differs from nucleic acids of the non-target species by at least a single nucleotide base. A first specific primer for the target nucleic acid and a second specific primer for the non-target species are added to the sample, along with a universal primer and a non-natural nucleotide base having a label. The sequence of each specific primer may differ from another at one terminus or near a terminus (e.g., within 1 base, 2 bases, 3 bases, or 4 bases from the terminus). The sequence of each specific primer may differ from another (e.g., by a single nucleotide, by two nucleotides, or by three nucleotides). Each specific primer may include an identical non-natural nucleotide base and a label (e.g., a fluorescent label, a radiolabel, and an enzyme label). Each label may be different from the other. For example, one label may be fluorescein (FAM) and the other label may be hexachlorofluorescein (HEX). Typically, the specific primers are tailed primers (i.e., primers with non-complementary nucleotides added to one end of the primer). The tails may be added to the 5' end of forward primers and to the 3' end of reverse primers. The tails may be designed to improve the specificity of the primers by reducing mispriming during PCR. For example, the tail sequences can be designed to add about 10° C. to the $T_m$ of the specific primers (e.g., to reduce "mispriming").

In some embodiments, the specific primers are allowed to anneal to the nucleic acids from the target and/or non-target species or subspecies. PCR using a nucleic acid polymerase (as herein described) is performed with chain extension of the annealed specific primer to form a double stranded product. One of the two strands of the product may incorporates a non-natural nucleotide base and the fluorescent label from the specific primer. As PCR progresses, the labeled strand is annealed with the universal primer, which in turn is extended in the opposite direction until the polymerase reaches the non-natural nucleotide base (e.g., isocytosine) and terminates extension with the addition of the complementary non-natural base (e.g., isoguanosine) bearing a fluorescent quencher such as dabcyl. PCR is run for the desired number of cycles to obtain this double-stranded amplification product. As more of the double stranded amplification product accumulates having both a fluorophore and a fluorescent quencher, the fluorescent signal from the specific primer(s) being incorporated into the amplified product will decrease. If only the target species or subspecies is present in the sample, only the fluorescent signal associated with the target nucleic acid will decrease. If only the non-target species or subspecies is present, only the fluorescent signal associated with the non-target nucleic acid will decrease. If both target and non-target species or subspecies are present, both signals will decrease as the PCR reaction progresses.

As will be apparent from the discussion herein, the relative sizes of the specific primers, as well as the amplified portion of the target and non-target nucleic acids, will vary depending upon the particular application. Further, the relative location of the primers along the target nucleic acid will vary. Additionally, the location of the non-natural base and labels used in the methods disclosed herein will vary depending upon application.

As used herein, *Neisseria gonorrhea* means the organism deposited at the American Type Culture Collection as Item No. 21825. "Non-gonococcal *Neisseria*" mean a microorganism belonging to the genus "*Neisseria*" which is not *Neisseria gonorrhea*. As used herein, non-gonococcal species of *Neisseria* may be referred to by ATCC Item No. including: *N. subflava* Item No. 19243; *N. perflava* Item No. 10555; *N. cinerea* Item No. 14685; *N. mucosa* Item No. 19693; *N. lactima* Item No. 23970; *N. polysaccharea* Item No. 43768; *N. flavescens* Item No. 13115; *N. dentrificans* Item No. 14686; *N. meningitides* 6250; and *N. sicca* Item No. 29193

In some embodiments, the methods and kits disclosed herein may utilize methods disclosed in U.S. published application no. 2002/0150900, which is incorporated herein by reference.

Polymerases

Disclosed herein are methods that may utilize the polymerase chain reaction, or a Fast-shot™ amplification, to detect nucleic acids of interest in a sample (i.e., nucleic acids of the target and non-target species or subspecies). Suitable nucleic acid polymerases include, for example, polymerases capable of extending an oligonucleotide by incorporating nucleic acids complementary to a template oligonucleotide. For example, the polymerase can be a DNA polymerase.

Enzymes having polymerase activity catalyze the formation of a bond between the 3' hydroxyl group at the growing end of a nucleic acid primer and the 5' phosphate group of a nucleotide triphosphate. These nucleotide triphosphates are usually selected from deoxyadenosine triphosphate (A), deoxythymidine triphosphate (T), deoxycytosine triphosphate (C) and deoxyguanosine triphosphate (G). However, in at least some embodiments, polymerases useful for the methods disclosed herein also may incorporate non-natural bases using nucleotide triphosphates of those non-natural bases.

Because the relatively high temperatures necessary for strand denaturation during methods such as PCR can result in the irreversible inactivation of many nucleic acid polymerases, nucleic acid polymerase enzymes useful for performing the methods disclosed herein preferably retain sufficient polymerase activity to complete the reaction when subjected to the temperature extremes of methods such as PCR. Preferably, the nucleic acid polymerase enzymes useful for the methods disclosed herein are thermostable nucleic acid polymerases. Suitable thermostable nucleic acid polymerases include, but are not limited to, enzymes derived from thermophilic organisms. Examples of thermophilic organisms from which suitable thermostable nucleic acid polymerase can be derived include, but are not limited to, *Thermus aquaticus, Thermus thermophilus, Thermus flavus, Thermotoga neapolitana* and species of the *Bacillus, Thermococcus, Sulfobus,* and *Pyrococcus* genera. Nucleic acid polymerases can be purified directly from these thermophilic organisms. However, substantial increases in the yield of nucleic acid polymerase can be obtained by first cloning the gene encoding the enzyme in a multicopy expression vector by recombinant DNA technology methods, inserting the vector into a host cell strain capable of expressing the enzyme, culturing the vector-containing host cells, then extracting the nucleic acid polymerase from a host cell strain which has expressed the enzyme. Suitable thermostable nucleic acid polymerases, such as those described above, are commercially available.

A number of nucleic acid polymerases possess activities in addition to nucleic acid polymerase activity; these can include 5'-3' exonuclease activity and 3'-5' exonuclease activity. The 5'-3' and 3'-5' exonuclease activities are known to those of ordinary skill in the art. The 3'-5' exonuclease activity improves the accuracy of the newly-synthesized strand by removing incorrect bases that have been incorporated. In contrast, the 5'-3' exonuclease activity often present in nucleic acid polymerase enzymes can be undesirable in a particular application since it may digest nucleic acids, including primers, that have an unprotected 5' end. Thus, a thermostable nucleic acid polymerase with an attenuated 5'-3' exonuclease activity, or in which such activity is absent, is a desired characteristic of an enzyme for use in at least some embodiments of the methods disclosed herein. In other embodiments, the polymerase is desired to have 5'-3' exonuclease activity to efficiently cleave the reporter and release labeled fragments so that the signal is directly or indirectly generated.

Suitable nucleic acid polymerases having no 5'-3' exonuclease activity or an attenuated 5'-3' exonuclease activity are known in the art. Various nucleic acid polymerase enzymes have been described where a modification has been introduced in a nucleic acid polymerase which accomplishes this object. For example, the Klenow fragment of E. coli DNA polymerase I can be produced as a proteolytic fragment of the holoenzyme in which the domain of the protein controlling the 5'-3' exonuclease activity has been removed. Suitable nucleic acid polymerases deficient in 5'-3' exonuclease activity are commercially available. Examples of commercially available polymerases that are deficient in 5'-3' exonuclease activity include AMPLITAQ STOFFEL™ DNA polymerase and KlenTaq™ DNA polymerase.

Polymerases can "misincorporate" bases during PCR. In other words, the polymerase can incorporate a nucleotide (for example adenine) at the 3' position on the synthesized strand that does not form canonical hydrogen base pairing with the paired nucleotide (for example, cytosine) on the template nucleic acid strand. The PCR conditions can be altered to decrease the occurrence of misincorporation of bases. For example, reaction conditions such as temperature, salt concentration, pH, detergent concentration, type of metal, concentration of metal, and the like can be altered to decrease the likelihood that polymerase will incorporate a base that is not complementary to the template strand.

As an alternative to using a single polymerase, any of the methods described herein can be performed using multiple enzymes. For example, a polymerase, such as an exo-nuclease deficient polymerase, and an exo-nuclease can be used in combination. Another example is the use of an exo-nuclease deficient polymerase and a thermostable flap endonuclease. In addition, it will be recognized that RNA can be used as a sample and that a reverse transcriptase can be used to transcribe the RNA to cDNA. The transcription can occur prior to or during PCR amplification.

Specific Primers

Disclosed herein are methods for detecting a target nucleic acid that may utilize PCR. The methods may involve a polymerase, a first primer and a second primer. In PCR techniques, the primers are designed to be complementary to sequences known to exist in a target nucleic acid to be amplified. Typically, the primers are chosen to be complementary to sequences that flank (and can be part of) the target nucleic acid sequence to be amplified. Preferably, the primers are chosen to be complementary to sequences that flank the target nucleic acid to be detected. Once the sequence of the target nucleic acid is known, the sequence of a primer is prepared by first determining the length or size of the target nucleic acid to be detected, determining appropriate flanking sequences that are near the 5' and 3' ends of the target nucleic acid sequence or close to the 5' and 3' ends, and determining the complementary nucleic acid sequence to the flanking areas of the target nucleic acid sequence using standard Watson-Crick base pairing rules, and then synthesizing the determined primer sequences. This preparation can be accomplished using any suitable methods known in the art, for example, cloning and restriction of appropriate sequences and direct chemical synthesis. Chemical synthesis methods can include, for example, the phosphotriester method described by Narang et al. (1979) Methods in Enzymology 68:90, the phosphodiester method disclosed by Brown et al. (1979) Methods in Enzymology 68:109, the diethylphosphoramidate method disclosed in Beaucage et al. (1981) Tetrahedron Letters 22:1859, and the solid support method disclosed in U.S. Pat. No. 4,458,066, all of which are incorporated herein by reference.

The ability of the first primer and second primer to form sufficiently stable hybrids to the target nucleic acid depends upon several factors, for example, the degree of complementarity exhibited between the primer and the target nucleic acid. Typically, an oligonucleotide having a higher degree of complementarity to its target will form a more stable hybrid with the target.

Additionally, the length of the primer can affect the temperature at which the primer will hybridize to the target nucleic acid. Generally, a longer primer will form a sufficiently stable hybrid to the target nucleic acid sequence at a higher temperature than will a shorter primer.

Further, the presence of high proportion of G or C or of particular non-natural bases in the primer can enhance the stability of a hybrid formed between the primer and the target nucleic acid. This increased stability can be due to, for example, the presence of three hydrogen bonds in a G-C interaction or other non-natural base pair interaction compared to two hydrogen bonds in an A-T interaction.

Stability of a nucleic acid duplex can be estimated or represented by the melting temperature, or "$T_m$." The $T_m$ of a particular nucleic acid duplex under specified conditions is the temperature at which 50% of the population of the nucleic acid duplexes dissociate into single-stranded nucleic acid molecules. The $T_m$ of a particular nucleic acid duplex can be predicted by any suitable method. Suitable methods for determining the $T_m$ of a particular nucleic acid duplex include, for example, software programs. Primers suitable for use in the methods and kits disclosed herein can be predetermined based on the predicted $T_m$ of an oligonucleotide duplex that comprises the primer.

When the first primer and second primer are annealed to the target nucleic acid, a gap exists between the 3' terminal nucleotide of the first primer and the 3' terminal nucleotide of the second primer. The gap comprises a number of nucleotides of the target nucleic acid. The gap can be any number of nucleotides provided that the polymerase can effectively incorporate nucleotides into an elongating strand to fill the gap during a round of the PCR reaction (e.g., a round of annealing, extension, denaturation). Typically, a polymerase can place about 30 to about 100 bases per second. Thus, the maximum length of the gap between primers depends upon the amount of time within a round of PCR where the temperature is in a range in which the polymerase is active and the primers are annealed.

For a Fast-shot™ amplification, using a standard thermal cycler, the temperature change is relatively slow given the limitations of the Peltier cooling and heating. When using a standard thermal cycler, the time the Fast-shot™ amplification reaction conditions are within a temperature range where the polymerase is active and the primer is annealed is about 10 to about 15 seconds. It is contemplated that the methods disclosed herein can be performed using a microfluidics system capable of rapidly thermal cycling the temperature of a sample, where extension times are relatively short and temperature change is relatively rapid. Such rapid thermal cycling can be performed using, for example, LabChip™ technology (Caliper Technology, Palo Alto, Calif.). In one embodiment, the first and second oligonucleotide primers are designed such that a gap of between about zero (0) to about five (5) bases on the target nucleic acid exists between the 3' ends of the PCR primers when annealed to the target nucleic acid.

Non-Natural Bases

As contemplated in the methods and kits disclosed herein, the second region of the second primer typically comprises at least one non-natural base. DNA and RNA are oligonucleotides that include deoxyriboses or riboses, respectively, coupled by phosphodiester bonds. Each deoxyribose or ribose includes a base coupled to a sugar. The bases incorporated in naturally-occurring DNA and RNA are adenosine (A), guanosine (G), thymidine (T), cytosine (C), and uridine (U). These five bases are "natural bases". According to the rules of base pairing elaborated by Watson and Crick, the natural bases can hybridize to form purine-pyrimidine base pairs, where G pairs with C and A pairs with T or U. These pairing rules facilitate specific hybridization of an oligonucleotide with a complementary oligonucleotide.

The formation of these base pairs by the natural bases is facilitated by the generation of two or three hydrogen bonds between the two bases of each base pair. Each of the bases includes two or three hydrogen bond donor(s) and hydrogen bond acceptor(s). The hydrogen bonds of the base pair are each formed by the interaction of at least one hydrogen bond donor on one base with a hydrogen bond acceptor on the other base. Hydrogen bond donors include, for example, heteroatoms (e.g., oxygen or nitrogen) that have at least one attached hydrogen. Hydrogen bond acceptors include, for example, heteroatoms (e.g., oxygen or nitrogen) that have a lone pair of electrons.

The natural bases, A, G, C, T, and U, can be derivatized by substitution at non-hydrogen bonding sites to form modified natural bases. For example, a natural base can be derivatized for attachment to a support by coupling a reactive functional group (for example, thiol, hydrazine, alcohol, amine, and the like) to a non-hydrogen bonding atom of the base. Other possible substituents include, for example, biotin, digoxigenin, fluorescent groups, alkyl groups (e.g., methyl or ethyl), and the like.

Non-natural bases, which form hydrogen-bonding base pairs, can also be constructed as described, for example, in U.S. Pat. Nos. 5,432,272; 5,965,364; 6,001,983; 6,037,120; U.S. published application no. 2002/0150900; and U.S. patent application Ser. No. 08/775,401, all of which are incorporated herein by reference. Suitable bases and their corresponding base pairs may include the following bases in base pair combinations (iso-C/iso-G, K/X, H/J, and M/N):

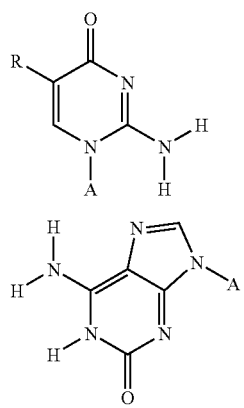

isoC isoG

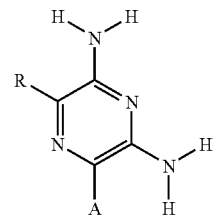

K

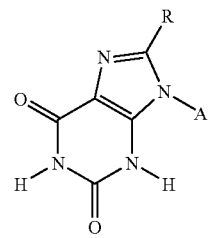

X

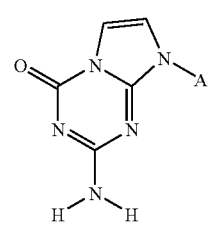

J

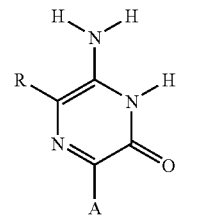

H

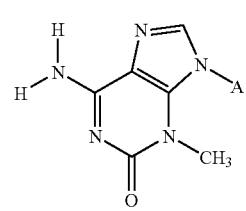

N

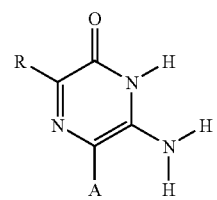

M where A is the point of attachment to the sugar or other portion of the polymeric backbone and R is H or a substituted or unsubstituted alkyl group. It will be recognized that other non-natural bases utilizing hydrogen bonding can be prepared, as well as modifications of the above-identified non-natural bases by incorporation of functional groups at the non-hydrogen bonding atoms of the bases.

The hydrogen bonding of these non-natural base pairs is similar to those of the natural bases where two or three hydrogen bonds are formed between hydrogen bond acceptors and hydrogen bond donors of the pairing non-natural bases. One of the differences between the natural bases and these non-natural bases is the number and position of hydrogen bond acceptors and hydrogen bond donors. For example, cytosine can be considered a donor/acceptor/acceptor base with guanine being the complementary acceptor/donor/donor base. Iso-C is an acceptor/acceptor/donor base and iso-G is the complementary donor/donor/acceptor base, as illustrated in U.S. Pat. No. 6,037,120, incorporated herein by reference.

Other non-natural bases for use in oligonucleotides include, for example, naphthalene, phenanthrene, and pyrene derivatives as discussed, for example, in Ren et al., *J. Am. Chem. Soc.* 118, 1671 (1996) and McMinn et al., *J. Am. Chem. Soc.* 121, 11585 (1999), both of which are incorporated herein by reference. These bases do not utilize hydrogen bonding for stabilization, but instead rely on hydrophobic or van der Waals interactions to form base pairs.

The use of non-natural bases according to the methods disclosed herein is extendable beyond the detection and quantification of nucleic acid sequences present in a sample. For example, non-natural bases can be recognized by many enzymes that catalyze reactions associated with nucleic acids. While a polymerase requires a complementary nucleotide to continue polymerizing an extending oligonucleotide chain, other enzymes do not require a complementary nucleotide. If a non-natural base is present in the template and its complementary non-natural base is not present in the reaction mix, a polymerase will typically stall (or, in some instances, misincorporate a base when given a sufficient amount of time) when attempting to extend an elongating primer past the non-natural base. However, other enzymes that catalyze reactions associated with nucleic acids, such as ligases, kinases, nucleases, polymerases, topoisomerases, helicases, and the like can catalyze reactions involving non-natural bases. Such features of non-natural bases can be taken advantage of, and are within the scope of the presently disclosed methods and kits.

For example, non-natural bases can be used to generate duplexed nucleic acid sequences having a single strand overhang. This can be accomplished by performing a PCR reaction to detect a target nucleic acid in a sample, the target nucleic acid having a first portion and a second portion, where the reaction system includes all four naturally occurring dNTP's, a first primer that is complementary to the first portion of the target nucleic acid, a second primer having a first region and a second region, the first region being complementary to the first portion of the target nucleic acid, and the second region being noncomplementary to the target nucleic acid. The second region of the second primer comprises a non-natural base. The first primer and the first region of the second primer hybridize to the target nucleic acid, if present. Several rounds of PCR will produce an amplification product containing (i) a double-stranded region and (ii) a single-stranded region. The double-stranded region is formed through extension of the first and second primers during PCR. The single-stranded region includes the one or more non-natural bases. The single-stranded region of the amplification product results because the polymerase is not able to form an extension product by polymerization beyond the non-natural base in the absence of the nucleotide triphosphate of the complementary non-natural base. In this way, the non-natural base functions to maintain a single-stranded region of the amplification product.

As mentioned above, the polymerase can, in some instances, misincorporate a base opposite a non-natural base. In this embodiment, the misincorporation takes place because the reaction mix does not include a complementary non-natural base. Therefore, if given sufficient amount of time, the polymerase can, in some cases, misincorporate a base that is present in the reaction mixture opposite the non-natural base.

Amplification

During PCR, the polymerase enzyme, first primer and second primer are used to generate an amplification product as described herein. One PCR technique that can be used is a modified PCR, or Fast-shot™ amplification. As used herein, the term "Fast-shot™ amplification" refers to a modified polymerase chain reaction.

Traditional PCR methods include the following steps: denaturation, or melting of double-stranded nucleic acids; annealing of primers; and extension of the primers using a polymerase. This cycle is repeated by denaturing the extended primers and starting again. The number of copies of the target sequence in principle grows exponentially. In practice, it typically doubles with each cycle until reaching a plateau at which more primer-template accumulates than the enzyme can extend during the cycle; then the increase in target nucleic acid becomes linear.

Fast-shot amplification is a modified polymerase chain reaction wherein the extension step, as well as the annealing and melting steps, are very short or eliminated. As used herein, when referring to "steps" of PCR, a step is a period of time during which the reaction is maintained at a desired temperature without substantial fluctuation of that temperature. For example, the extension step for a typical PCR is about 30 seconds to about 60 seconds. The extension step for a Fast-shot™ amplification typically ranges from about 0 seconds to about 20 seconds. Preferably, the extension step is about 1 second or less. In a preferred embodiment, the extension step is eliminated. The time for annealing and melting steps for a typical PCR can range from 30 seconds to 60 seconds. The time for annealing and melting steps for a Fast-shot™ amplification generally can range from about 0 seconds to about 60 seconds. For Fast-shot™ amplification, the annealing and melting steps are typically no more than about 2 seconds, preferably about 1 second or less. When the extension step is eliminated, the temperature is cycled between the annealing and melting steps without including an intermediate extension step between the annealing and melting temperatures.

Additionally, the limit of how quickly the temperature can be changed from the annealing temperature to the melting temperature depends upon the efficiency of the polymerase in incorporating bases onto an extending primer and the number of bases it must incorporate, which is determined by the gap between the primers and the length of the primers. Examples of Fast-shot™ amplification are shown in the Examples.

The number of Fast-shot™ amplification cycles required to determine the presence of a nucleic acid sequence in a sample can vary depending on the number of target molecules in the sample. In one of the examples described below, a total of 37 cycles was adequate to detect as little as 100 target nucleic acid molecules.

Amplification Products

PCR may be used to generate an amplification product (i.e., an amplicon) comprising a double-stranded region and a single-stranded region. The double-stranded region may result from extension of the first and second primers. As discussed above, the single-stranded region may result from incorporation of a non-natural base in the second primer of the disclosed methods. A region of the first and/or second primer may not be complementary to the target nucleic acid. Because the non-natural base follows base-pairing rules of Watson and Crick and forms bonds with other non-natural bases, as discussed above, the presence of a non-natural base may maintain a region as a single-stranded region in the amplification product.

In an alternative embodiment, the single-stranded region comprises more than one non-natural base. The number of non-natural bases included in the first and/or second primer can be selected as desired.

Labels

In accordance with the methods and kits disclosed herein, the specific primers and the added non-natural nucleotide base may comprises a label. Nucleotides and oligonucleotides can be labeled by incorporating moieties detectable by spectroscopic, photochemical, biochemical, immunochemical, or chemical assays. The method of linking or conjugating the label to the nucleotide or oligonucleotide depends on the type of label(s) used and the position of the label on the nucleotide or oligonucleotide.

A variety of labels which are appropriate for use in the methods and kits, as well as methods for their inclusion in the probe, are disclosed herein and are known in the art. These include, but are not limited to, enzyme substrates, radioactive atoms, fluorescent dyes, chromophores, chemiluminescent labels, electrochemiluminescent labels, such as ORI-TAG™ (Igen), ligands having specific binding partners, or any other labels that can interact with each other to enhance, alter, or diminish a signal. It is understood that, should the PCR be practiced using a thermocycler instrument, a label should be selected to survive the temperature cycling required in this automated process.

One radioactive atom suitable for a label according to the disclosed methods and kits is $^{32}P$. Methods for introducing $^{32}P$ into nucleic acids are known in the art, and include, for example, 5' labeling with a kinase, or random insertion by nick translation.

It should be understood that the above description is not meant to categorize the various labels into distinct classes, as the same label can serve in several different modes. For example, $^{125}I$ can serve as a radioactive label or as an electron-dense reagent. Further, one can combine various labels for desired effects. For example, one could label a nucleotide with biotin, and detect its presence with avidin labeled with $^{125}I$. Other permutations and possibilities will be apparent to those of ordinary skill in the art, and are considered within the scope of the present methods and kits.

In some situations, it is desirable to use two interactive labels on a single oligonucleotide with due consideration given for maintaining an appropriate spacing of the labels on the oligonucleotide to permit the separation of the labels during oligonucleotide hydrolysis. It can be similarly desirable to use two interactive labels on different oligonucleotides, such as, for example, the reporter and the second region of the second primer. In this embodiment, the reporter and the second region are designed to hybridize to each other. Again, consideration is given to maintaining an appropriate spacing of the labels between the oligonucleotides when hybridized.

One type of interactive label pair is a quencher-dye pair. Preferably, the quencher-dye pair is comprised of a fluorophore and a quencher. Suitable fluorophores are described herein and may include, but are not limited to fluorescein, cascade blue, hexachloro-fluorescein, tetrachloro-fluorescein, TAMRA, ROX, Cy3, Cy3.5, Cy5, Cy5.5, 4,4-difluoro-5,7-diphenyl-4-bora-3a,4a-diaza-s-indacene-3-propionic acid, 4,4-difluoro-5,p-methoxyphenyl-4-bora-3a,4a-diaza-s-indacene-3-propionic acid, 4,4-difluoro-5-styryl-4-bora-3a,4-adiaza-S-indacene-propionic acid, 6-carboxy-X-rhodamine, N,N,N',N'-tetramethyl-6-carboxyrhodamine, Texas Red, Eosin, fluorescein, 4,4-difluoro-5,7-diphenyl-4-bora-3a,4a-diaza-s-indacene-3-propionic acid, 4,4-difluoro-5,p-ethoxyphenyl-4-bora-3a,4a-diaza-s-indacene 3-propionic acid and 4,4-difluoro-5-styryl-4-bora-3a,4a-diaza-S-indacene-propionic acid. Suitable quenchers include, for example, Dabcyl, QSY7™ (Molecular Probes, Eugene, Oreg.) and the like. In addition, dyes can also be used as a quencher if they absorb the emitted light of another dye.

The labels can be attached to the nucleotides, including non-natural bases, or oligonucleotides directly or indirectly by a variety of techniques. Depending upon the precise type of label used, the label can be located at the 5' or 3' end of the reporter, located internally in the reporter's nucleotide sequence, or attached to spacer arms extending from the reporter and having various sizes and compositions to facilitate signal interactions. Using commercially available phosphoramidite reagents, one can produce oligonucleotides containing functional groups (e.g., thiols or primary amines) at either terminus, for example by the coupling of a phosphoramidite dye to the 5' hydroxyl of the 5' base by the formation of a phosphate bond, or internally, via an appropriately protected phosphoramidite, and can label them using protocols described in, for example, PCR Protocols: A Guide to Methods and Applications, ed. by Innis et al., Academic Press, Inc., 1990, incorporated herein by reference.

Methods for incorporating oligonucleotide functionalizing reagents having one or more sulfhydryl, amino or hydroxyl moieties into the oligonucleotide reporter sequence, typically at the 5' terminus, are described in U.S. Pat. No. 4,914,210, incorporated herein by reference. For example, 5' phosphate group can be incorporated as a radioisotope by using polynucleotide kinase and $[\gamma^{32}P]ATP$ to provide a reporter group. Biotin can be added to the 5' end by reacting an aminothymidine residue, introduced during synthesis, with an N-hydroxysuccinimide ester of biotin.

Labels at the 3' terminus, for example, can employ polynucleotide terminal transferase to add the desired moiety, such as for example, cordycepin, $^{35}S$-dATP, and biotinylated dUTP.

Oligonucleotide derivatives are also available as labels. For example, etheno-dA and etheno-A are known fluorescent adenine nucleotides which can be incorporated into a reporter. Similarly, etheno-dC is another analog that can be used in reporter synthesis. The reporters containing such nucleotide derivatives can be hydrolyzed to release much more strongly fluorescent mononucleotides by the polymerase's 5' to 3' nuclease activity as nucleic acid polymerase extends a primer during PCR.

In some embodiments, the labeled reporter comprises first and second labels wherein the first label is separated from the second label by a nuclease-susceptible cleavage site.

The label of the reporter can be positioned at any suitable location of the reporter. For example, when the reporter comprises more than one nucleotide, the label can be attached to any suitable nucleotide of the reporter sequence. The label can be positioned at the 5' terminus of the reporter and separated from the reporter sequence that is complementary to the target nucleic acid by a non-complementary sequence. In this embodiment, the reporter comprises a non-natural base that is complementary to the non-natural base of the amplification product, and a sequence that is noncomplementary to the second region of the second primer, and the label is positioned in the sequence that is noncomplementary to the second region. Further, the label can be indirectly attached to a nucleotide of the reporter, using a suitable spacer or chemical linker.

In another embodiment, the labeled reporter comprises a pair of interactive signal-generating labels effectively positioned on the reporter or on the reporter and a second componenet of the assay (such as the second oligonucleotide) so as to quench the generation of detectable signal when the interactive signal-generating labels are in sufficiently close proximity to each other. Preferably, the labels are separated by a site within the reporter that is susceptible to nuclease cleavage, thereby allowing the 5' to 3' nuclease activity of the nucleic acid polymerase to separate the first interactive signal-generating label from the second interactive signal-generating label by cleaving the reporter at the nuclease susceptible site. Separation of the interactive signal-generating moieties (e.g., cleavage of the reporter to release a reporter fragment containing one of the labels) results in the production of a detectable signal. Examples of such labels include dye/quencher pairs or two dye pairs (where the emission of one dye stimulates emission by the second dye).

In an exemplified embodiment, the interactive signal generating pair comprises a fluorophore as described herein, which may include fluorescein, 5-[(2-aminoethyl)amino] napthalene-1-sulfonic acid (EDANS), tetramethylrhodamine, or the like, and a quencher that can quench the fluorescent emission of the fluorophore, as described herein. For example, a quencher may include dimethylaminoazobenzen aminoexal-3-acryinido (Dabcyl). The ordinarily skilled artisan can select a suitable quencher moiety that will quench the emission of the particular fluorophore. In the exemplified embodiment, the Dabcyl quencher absorbs the emission of fluorescence from the fluorophore moiety. Fluorophore-quencher pairs have been described in Morrison, Detection of Energy Transfer and Fluorescence Quenching in Nonisotopic Probing, Blotting and Sequencing Academic Press, 1995, incorporated herein by reference.

Alternatively, these interactive signal-generating labels can be used in a detection method where the second region of the second primer comprises at least one non-natural base and a label. The second label of the pair is provided by the reporter, which comprises at least one non-natural base that is complementary to the non-natural base of the second primer, and a second label. For example, if a dye/quencher pair is used, hybridization of the reporter to or incorporation of the amplification product will result in a reduction of fluorescence.

Alternatively, the proximity of the two labels can be detected using fluorescence resonance energy transfer (FRET) or fluorescence polarization. FRET is a distance-dependent interaction between the electronic excited states of two dye molecules in which excitation is transferred from a donor molecule to an acceptor molecule without emission of a photon. Examples of donor/acceptor dye pairs for FRET are known in the art and may include fluorophores and quenchers described herein such as Fluorescein/Tetramethylrhodamine, IAEDANS™/Fluorescein (Molecular Probes, Eugene, Oreg.), EDANS™/Dabcyl, Fluorescein/Fluorescein (Molecular Probes, Eugene, Oreg.), BODIPY™ FL/BODIPY™ FL (Molecular Probes, Eugene, Oreg.), and Fluorescein/QSY7™.

Annealing

The reporter is added to the sample at an appropriate time during the detection method. After PCR has produced sufficient amplification product, the reporter may be annealed to the single stranded region of the amplification product. In this some embodiments, the reporter comprises a dye, a quencher, and a non-natural base that is complementary to the non-natural base of the first and/or second primer. The reporter anneals to the sequence of the first and/or second primer comprising the non-natural base. The reporter can be added to the reaction mix after PCR has produced sufficient amplification product, or the reporter can be added to the reaction mix prior to PCR amplification. Preferably, the reporter is added to the reaction mix prior to PCR amplification. After amplification, the temperature is preferably lowered to a temperature lower than the melting temperature of the reporter/amplification product to allow annealing of the reporter to the single-stranded region of the amplification product. In one embodiment, the reaction temperature is lowered to about 49° C. or less during the step of annealing the reporter to the single-stranded overhang region. Annealing is performed similarly for other embodiments of the methods and kits including those using other reporters and other types of labels, as described above. In another embodiment, the reporter is annealed at or above the melting temperature of the first and second primers and the amplification product. This embodiment may be performed in "real time" detection of the PCR amplification product Cleaving In some embodiments of the methods and kits, after the reporter anneals to the amplification product, a cleavage event occurs to release at least one reporter fragment. The release of the reporter fragment is correlated with the presence of the target nucleic acid, as described below. Once the reporter anneals to the single-stranded region of the amplification product, this forms a reporter/amplification product complex that is recognizable by an enzyme that cleaves the complex to release the reporter fragment. The enzymes contemplated for use in this embodiment are generally capable of recognizing a variety of reporter/amplification product complex structures. For example, the 5' end portion of the reporter can overlap with a sequence of the amplification product, forming a single-stranded overhang region.

In another embodiment, the reporter does not contain an overlapping region to form a single-stranded overhang region, but rather the reporter forms a nick-like structure when it is annealed to the amplification product. In this embodiment, a nick-like structure is formed in the amplification product. Generally, a "nick" in duplex DNA means the absence of a phophodiester bond between two adjacent nucleotides on one strand. As used herein, a "nick-like" structure is formed when there is an absence of the phosphodiester bond between the 5' terminal nucleotide of the reporter and the 3' terminal nucleotide of the strand of the amplification product. There are several enzymes, such as, for example, *E. coli* DNA polymerase I, that are capable of using a nick in duplex DNA as the starting point from which one strand of duplex DNA can be degraded and replaced by resynthesis of new material.

In some embodiments, the reporter includes one or more of: a non-natural base (which is complementary to the non-natural base of the amplification product), a dye, and a quencher. The reporter anneals to a single-stranded portion of the amplification product. Therefore, a nick is produced between the non-natural base and the adjacent nucleotide of the amplification product. In this embodiment, the polymerase recognizes the nick-like structure formed in the reporter/amplification product complex and cleaves the reporter at that nick site. Cleavage of the complex releases the reporter fragment, and a signal is detected.

While some of the particular structures formed by the reporter/amplification product complex will be discussed in some detail, other reporter/amplification product complexes can be formed to achieve cleavage as described herein.

After annealing, a portion of the 5' end of a reporter may not be annealed to the target and may be single-stranded. It is understood that any length, in bases, of the single-stranded overhang region is contemplated, provided that the ability of the 5' to 3' nuclease activity of the polymerase to cleave annealed reporter fragments from the amplification product is maintained. For detection, the reaction is continued under conditions sufficient to allow the 5' to 3' nuclease activity of the polymerase to cleave the annealed reporter. Cleavage of the reporter produces cleavage fragments (containing the label or a part of the label) which can then be detected (or, alternatively, the remaining reporter/amplification product complex can be detected) and which are indicative of the presence of the target nucleic acid in the sample. In at least some embodiments, the reporter fragments can include a mixture of mono-, di-, and larger nucleotide fragments.

The nuclease activity of the polymerase cleaves a single-stranded region, releasing a reporter fragment. In some embodiments, the reporter fragment comprises a dye. Release of the dye from the amplification product that includes a quencher allows detection of the dye. Therefore, release of the reporter fragment allows detection of the dye as it is released from proximity to the quencher. This, in turn, allows for correlation of the release of the reporter fragment with presence of the target nucleic acid. If instead, the placement of the dye and quencher are reversed and the quencher is released with the reporter fragment, the dye on the reporter/amplification product is then detected.

Incorporation of Non-Natural Bases

In some embodiments, a region of the first and/or second primer comprises a non-natural base. A non-natural base that is complementary to the non-natural base present in the first and/or second primer is incorporated into the amplification product using a suitable enzyme. In this embodiment, the incorporation of the non-natural base is correlated with the presence of the target nucleic acid in the sample.

The disclosed methods and kits may employ a reporter; a nucleic acid polymerase (not shown); a first primer and a second primer. The PCR reaction mixture may include the four naturally occurring deoxynucleotide triphosphates (i.e., dATP, dCTP, dGTP, and dTTP) as well as one or more non-natural nucleotide triphosphate (or an oligonucleotide containing a non-natural nucleotide triphosphate) as the reporter. In some embodiments, the one or more non-natural nucleotide triphosphates in the reaction mixture comprises a label, which may include a dye and/or a quencher. The PCR reaction mixture may be useful for performing Fast-shot™ amplification.

The first primer may comprise a sequence complementary to a portion of a target nucleic acid and can hybridize to that portion of the target nucleic acid. The second primer may have a first region and a second region. The first region may comprises a sequence complementary to a portion of the target sequence. The second region of the second primer may comprise a sequence that is not complementary to the target nucleic acid and may comprise at least one non-natural base. It will be understood that the second region can include additional nucleotides. Preferably, the non-natural base is located at the junction between the first region and the second region of the second primer. In some embodiments, the non-natural base present in the second region of the second oligonucleotide primer is an iso-C or an iso-G.

In addition to the first primer and second primer, the sample is reacted or contacted with a polymerase (not shown), and a polymerase chain reaction is performed. If the target nucleic acid is present in the sample, the complementary portion of the first primer and the complementary portion of the second primer anneal to the corresponding regions of the target nucleic acid following standard base-pairing rules. When the primers are annealed to the target, the 3' terminal nucleotide of the first primer is separated from the 3' terminal nucleotide of the second primer by a sequence of nucleotides, or a "gap." In a preferred embodiment, the first and second primers are designed such that gap of between about zero (0) to about five (5) bases on the template nucleic acid exists between the 3' ends of the PCR primers when annealed to the template nucleic acid.

The polymerase is used to synthesize a single strand from the 3'-OH end of each primer, using polymerase chain reaction, or a modified Fast-shot™ amplification. The polymerase chain reaction is allowed to proceed for the desired number of cycles, to obtain an amplification product.

The amplification product may include a double-stranded region and a single-stranded region, which comprises the at least one non-natural base of the second primer.

The amplification product may be contacted with a reporter. The reporter may comprises a label and at least one non-natural base. The reporter may be incorporated into the amplification product opposite the non-natural base. In some embodiments, the non-natural base of the reporter comprises a nucleotide triphosphate base that is complementary to the non-natural base of the single-stranded region of the amplification product. In this embodiment, the PCR reaction includes the presence of labeled non-natural nucleotide triphosphate base, in addition to the four naturally occurring nucleotide triphosphate bases (i.e., dATP, dCTP, dGTP, and dTTP). The concentration of non-natural nucleotide triphosphate base in the PCR reaction can range, for example, from 1 µM to 100 µM. The non-natural nucleotide triphosphate base may include a label.

Suitable enzymes for incorporation of the reporter into the amplification product include, for example, polymerases and ligases. A number of polymerases that are capable of incorporating natural nucleotides into an extending primer chain can also incorporate a non-natural base into an amplification product opposite a complementary non-natural base. Typically, class A DNA polymerases; such as Klenow, Tfl, Tth, Taq, Hot Tub, and Bst, are better able than class B polymerases; such as Pfu, Tli, Vent exo-, T4, and Pwo, to incorporate a non-natural base. Reverse transcriptases, such as HIV-1, can also be used to incorporate non-natural bases into an extending primer opposite its complementary non-natural base within a template. In this embodiment the polymerase can be nuclease deficient or can have reduced nuclease activity. While not intended to limit the disclosed methods and kits, nuclease deficient polymerases are expected to be more robust because nuclease activities have been shown to interfere with some PCR reactions (Gene 1992 112(1):29-35 and Science 1993 260(5109):778-83).

Presence of the target nucleic acid in the sample is determined by correlating the presence of the reporter in the amplification product. Suitable detection and visualization methods are used to detect the target nucleic acid. For example, presence of the target nucleic acid may be determined by detecting the label by fluorescence or other visualization method. Fluorescence polarization, for example, can be used to detect the incorporation of the reporter into the amplification product.

Preferably, in some embodiments, a washing step or a separation step is performed after incorporation of the reporter into the amplification product, and prior to detection. This washing or separation step will remove unbound or unincorporated reporter from the system, so that detection of signal is dependent upon incorporated reporter. One of skill in the art would readily appreciate that any known washing or separation steps can be used in connection with the disclosed methods and kits, including size separation by gel electrophoresis, and the like. Alternatively, a washing step may not be needed when fluorescence polarization is used as the method of detection.

The reporter used in this embodiment comprises at least one non-natural base. The non-natural base(s) of the reporter preferably include a label. The non-natural base(s) of the reporter is capable of being inserted by the polymerase into the amplification product opposite to the at least one non-natural base of the second primer during the PCR amplification.

In other embodiments, the reporter comprises a non-natural base (which is complementary to a non-natural base present in the first and/or second primer), and a quencher. In this embodiment, the non-natural base of the first and/or second primer includes a dye. In this embodiment, incorporation of the reporter brings the quencher into proximity with the dye. This, in turn, reduces the signal output of the dye, and this reduction in signal can be detected and correlated with the presence of the target nucleic acid. Suitable dye-quencher pairs are discussed above. Alternatively, a dye-dye pair can be used for fluorescence induction. When the target nucleic acid is present, PCR creates a duplexed product that places the two dyes in close proximity, and the fluorescent output of the label changes. The change is detectable by bench-top fluorescent plate readers.

The polymerase used in this embodiment can have nuclease activity, can have reduced nuclease activity, or can be nuclease deficient. Preferably, the polymerase is a thermostable polymerase.

Detection

Detection and analysis of the reporter (or oligonucleotide fragments thereof) can be accomplished using any methods known in the art. Numerous methods are available for the detection of nucleic acids containing any of the above-listed labels. For example, biotin-labeled oligonucleotide(s) can be detected using non-isotopic detection methods which employ avidin conjugates such as streptavidin-alkaline phosphatase conjugates. Fluorescein-labeled oligonucleotide(s) can be detected using a fluorescein-imager.

In one embodiment the reporter oligonucleotides can be detected within the PCR reaction mixture without any further processing. For example, the signal from cleaved oligonucleotides can be resolved from that of uncleaved oligonucleotides without physical separation. This can be accomplished, for example by fluorescence polarization analysis where a change in size and therefore rate of rotation in solution of fluorescent molecules can be detected.

In one embodiment, when the target is present, a duplexed product is created that places the first and second labels (e.g. dye/dye pair) into close proximity. When the two labels are in close proximity, the fluorescent output of the reporter molecule label changes. The change is detectable by most benchtop fluorescent plate readers. Alternatively, the label pair comprises a quencher-label pair in close proximity. In this embodiment, the fluorescent output of the reporter molecule label changes, and this change is detectable. Other suitable detection methods are contemplated for used in the disclosed methods and kits.

In another embodiment, the reporter is detected after further processing. It is contemplated that the reporter oligonucleotide fragments can be separated from the reaction using any of the many techniques known in the art useful for separating oligonucleotides. For example, the reporter oligonucleotide fragments can be separated from the reaction mixture by solid phase extraction. The reporter oligonucleotide fragments can be separated by electrophoresis or by methods other than electrophoresis. For example, biotin-labeled oligonucleotides can be separated from nucleic acid present in the reaction mixture using paramagnetic or magnetic beads, or particles which are coated with avidin (or streptavidin). In this manner, the biotinylated oligonucleotide/avidin-magnetic bead complex can be physically separated from the other components in the mixture by exposing the complexes to a magnetic field. In one embodiment, reporter oligonucleotide fragments are analyzed by mass spectrometry.

In some embodiments, when amplification is performed and detected on an instrument capable of reading fluorescence during thermal cycling, the intended PCR product from non-specific PCR products can be differentiated. Amplification products other than the intended products can be formed when there is a limited amount of template nucleic acid. This can be due to a primer dimer formation where the second primer 108 is incorporated into a primer dimer with itself or the first primer 106. During primer dimer formation the 3' ends of the two primers hybridize and are extended by the nucleic acid polymerase to the 5' end of each primer involved. This creates a substrate that when formed is a perfect substrate for the primers involved to exponentially create more of this non-specific products in subsequent rounds of amplification. Therefore, the initial formation of the primer dimer does not need to be a favorable interaction since even if it is a very rare event the amplification process can allow the dimer product to overwhelm the reaction, particularly when template nucleic acid is limited or absent. When the first and/or second oligonucleotide primer is incorporated into this product a labeled nonstandard base is placed orthogonal to the nonstandard base of the second primer. This results in an interaction between the labels of the reporter and of the first and/or second primer which may give a detectable fluorescent change upon melting. Primer dimer products are typically shorter in length than the intended product and therefore have a lower melting temperature. Since the labels are held in close proximity across the duplex an event that would separate the two strands would disrupt the interaction of the labels. Increasing the temperature of the reaction which contains the reaction products to above the $T_m$ of the duplexed DNAs of the primer dimer and intended product may melt the DNA duplex of the product and disrupt the interaction of the labels giving a measurable change in fluorescence. By measuring the change in fluorescence while gradually increasing the temperature of the reaction subsequent to amplification and signal generation it may be possible to determine the $T_m$ of the intended product as well as that of the nonspecific product.

Nested PCR

Nested PCR can be performed using the disclosed methods and kits. By way of example, nested PCR can be performed using a first, second, and third primers (or more). The second primer has a first region complementary to the target sequence and a second region complementary to the reporter oligonucleotide. The first and third primers can hybridize to the target at higher temperatures than the second primer. A first amplification product can be produced after several PCR cycles are performed where cycling between denaturation and annealing temperatures allows annealing of the first and third primer to the target nucleic acid, but not the second primer. The PCR annealing temperature can subsequently be reduced to allow the first region of the second primer to hybridize to the first amplification product. Several cycles of PCR at the reduced annealing temperature can produce a second amplification product between the first and second primers. The temperature can be lowered to allow hybridization of the reporter oligonucleotide to the second region of the second primer.

Use in Detection of DNA Polymorphisms

The disclosed methods and kits are useful for detecting sequence variations in nucleic acid sequences. As used herein, "sequence variation" refers to differences in nucleic acid sequence between two nucleic acids. For example, a wild-type gene and a mutant form of this gene can vary in sequence by the presence of single base substitutions or deletions or insertions of one or more nucleotides. These two forms of the gene are said to vary in sequence from one another. One example of sequence variation is DNA polymorphisms. In some embodiments, detection of a single nucleotide polymorphism (SNP) using PCR and requiring no further sample manipulation other than placing the PCR reaction plate onto a fluorescence plate reader is performed. Specific reporters or primers are used which contain a specific label. For example, a system for detecting multiple target nucleic acids might include specific reporters or primers with labels having different colors (e.g., two different fluorescent labels, three different fluorescent labels, or four different fluorescent labels). In a system for detecting two targets with two fluorescent labels, the presence of either color may indicate the presence of the respective target in the sample and the presence of the combination of the two colors may indicate that both targets are present in the sample.

In some embodiments, two or more primers are designed to detect a single nucleotide variation (e.g., substitution, deletion, or insertion) as follows. Preferably, one of the primers used comprises a specific primer. Preferably, one of the primers comprises a non-natural base. In one embodiment, both of these features are provided by a single primer. Alternatively, the specific primer is a separate primer from the primer that comprises a non-natural base.

The specific primers that can be used to discriminate the target nucleic acids may be designed to be complementary to each target such that the polymorphic base of interest is positioned at the 3' end of the primer or near the 3' end of the primer (e.g., within 1, 2, 3, 4, or 5 bases of the 3' end of the primer). High levels of target discrimination may be achieved in part by the limited ability of selected polymerases to extend a primer which has a nucleotide mismatch at its 3' end or near its 3' end (e.g., within 1, 2, 3, 4, or 5 bases of the 3' end of the primer) relative to a non-specific target. Additionally, target discrimination can be accomplished by placing the mismatch at other positions in the specific primer. Generally, the specific position can be anywhere within the primer provided that the primer cannot specifically hybridize to the target or the polymerase cannot efficiently extend the primer if there is a mismatch. Preferably, the primers are chosen so that the mismatch sufficiently destabilizes hybridization of the specific primer to a non-specific target nucleic acid for the selected PCR conditions. In one embodiment, the specific position is within about 5 bases from the 3'-end of the primer. For example, the specific position can be at the 3'-terminal base of the primer. These alternate positions for the specific position in the primer can be used to achieve selective amplification in two primary ways: 1) by lowering the $T_m$ of the primer so that it is not hybridized on the template DNA during thermal cycling for the polymerase to extend, or 2) by creating an unfavorable primer/template structure that the polymerase will not extend. Enhanced specificity may be achieved by selecting suitable amplification conditions. For example, enhanced specificity may be achieved by using Fast-shot™ amplification cycles where the extension stop time, as well as the stop times for annealing and melting, are brief or non-existent. In one such embodiment, the reactions are rapidly cycled between about 90-100° C. and about 50-65° C. with a maximum of about a one-second hold at each temperature, thereby leaving the polymerase little time to extend mismatched primers. In an exemplified embodiment, the reaction is cycled between about 95° C. and about 58° C. with about a one second hold at each temperature. This rapid cycling is made possible by generating the shortest possible PCR product by, in general, leaving a gap of about zero (0) to about five (5) bases on the template nucleic acid between the 3' bases of the PCR primers. Preferably, the primers are designed to have the shortest sequence possible and a $T_m$ of approximately 55-60° C. In one embodiment involving SNP analysis on genomic DNA samples a total of about 37 cycles was adequate to detect as little as 30 target molecules.

Kits

Reagents employed in the disclosed methods can be packaged into diagnostic kits. Diagnostic kits include at least a first and second. In some embodiments the kit includes non-natural bases capable of being incorporated into an elongating oligonucleotide by a polymerase. In one embodiment, the non-natural bases are labeled. If the oligonucleotide and non-natural base are unlabeled, the specific labeling reagents can also be included in the kit. The kit can also contain other suitably packaged reagents and materials needed for amplification, for example, buffers, dNTPs, or polymerizing enzymes, and for detection analysis, for example, enzymes and solid phase extractants.

Reagents useful for the disclosed methods can be stored in solution or can be lyophilized. When lyophilized, some or all of the reagents can be readily stored in microtiter plate wells for easy use after reconstitution. It is contemplated that any method for lyophilizing reagents known in the art would be suitable for preparing dried down reagents useful for the disclosed methods.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

The present methods and kits, thus generally described, will be understood more readily by reference to the following examples, which are provided by way of illustration and are not intended to be limiting of the present methods and kits.

EXAMPLES

All percentages are by weight and all solvent mixture proportions are by volume unless otherwise noted.

Example 1

Primer Design

The symbols indicated in the sequence of the nucleic acid components are as follows: A=deoxyadenylate; T=deoxythymidylate; C=deoxycytidylate; G=deoxyguanylate; X=deoxy-iso-cytosine (d-isoC); Y=deoxy-iso-guanine (d-isoG); P=nucleotide of first primer complementary to polymorphic nucleotide in target nucleic acid; B=3' modification of reporter nucleic acid by addition of BiotinTEG CPG (Glen Research, Sterling, Va.) to 3' end that functions to block nucleic acid polymerase and extension of the reporter; Q=signal quenching element (5'-5-[(N-4'-carboxy-4(dimethylamino)-azobenzene)-aminohexyl-3-acrylimido]-2'-deoxyUridine (Dabcyl dT; Glen Research, Sterling, Va.) incorporated into reporter by addition of 5'-Dimethoxytrityloxy-5-[(N-4'-carboxy-4(dimethylamino)-azobenzene)-aminohexyl-3-acrylimido]-2'-deoxyUridine -3'-[(2-cyanoethyl)-(N,N-diisopropyl)]-phosphoramidite (Dabcyl dT; Glen Research, Sterling, Va.); FAM=Signal generating element (6-carboxyfluorescein (6-FAM); Glen Research, Sterling, Va.). Underlining indicates the portion of the nucleic acid component that is not complimentary to the template.

Example 2

Target Specific PCR

The working concentration (1×) of components in an exemplary PCR reaction for individual 20 μl PCR reaction volumes is shown below:

| Component | 1X Conc. |
|---|---|
| Tris pH 8.0 | 10 mM |
| Bovine Serum Albumin | 0.01% |
| Triton ™ X-100 | 0.01% |
| Herring Sperm DNA | 0.1 μg/ml |
| Potassium acetate | 40 mM |
| MgCl$_2$ | 2 mM |
| DNA polymerase | 1 U/rxn |
| dATP | 50 μM |
| dGTP | 50 μM |
| dCTP | 50 μM |
| dTTP | 50 μM |
| Primer(s) | 0.2 μM |
| Reporter (e.g., labeled diGTP) | 0.4 μM |

All components are thawed on ice and gently mixed together. A 10×PCR Buffer is prepared and composed of 100 mM Tris pH 8.0, 0.1% BSA, 0.1% Triton X-100, 1 mg/ml degraded herring sperm DNA (Sigma D-3159), 400 mM potassium acetate, and 20 mM MgCl$_2$. A master mix and an target specific mix re prepared by adding the reagents in the exemplarly proportions indicated below:

| Master Mix | | |
|---|---|---|
| Component | Volume per Reaction (μL) | Concentration in Reaction |
| dH$_2$O | 11.36 | — |
| 10X PCR Buffer | 2 | 1X |
| dNTPs 25 mM | 0.04 | 50 μM |
| Reporter | 0.2 | 0.4 μM |
| Second Primer | 0.2 | 0.2 μM |
| DNA polymerase | 0.2 | 1 U |

The final volume of the reaction is 20 μL. Five microliters of target nucleic acid is added to 15 μL of the combined Master Mix and first primer. The target nucleic acid volume may be increased or decreased according to end user needs by adjusting the amount of water added in the Master Mix. Five microliters may be a convenient volume to deliver with a multichannel pipetor. The Target Specific Mixes may be prepared as shown below:

| Target Specific Mixes | | |
|---|---|---|
| Component | Volume per Reaction (μL) | Concentration in Reaction |
| First Primer | 1 | 0.2 μM |
| Master Mix | 14 | — |

The assay plates may be prepared as follows: Fifteen microliters of a target specific mix (as defined above) is aliquoted into a 96-well assay plate. (A target specific mix may be prepared and run for each specific first primer that is to be used in the assay). The target nucleic acid samples are added in duplicate in a volume of 5 μL to each well containing a target specific mix. A certain number of wells are reserved as controls; a negative control (no target nucleic acid) should be run with each of the target specific mixes. Subsequent to the target nucleic acid addition, the reactions are overlaid with 20 μL of mineral oil and the assay plate is transferred to a DNA thermal cycler. Hands on time of this procedure is greatly reduced by the use of a multichannel pipetor.

Exemplary thermal cycling parameters for the assay plates are shown below:

| Cycle # | Step | Temp | Time |
|---|---|---|---|
| 1 | 1 | 95° C. | 12 min. |
| 2-38 | 1 | 95° C. | 1 sec. |
|  | 2 | 58° C. | 1 sec. |
| 39 | 1 | 49° C. | 20 min. |

Following PCR cycling reactions, the assay plates are tested for emission of a fluorescence signal. The assay plates are transferred to a PerSeptive Biosystems Cytofluor™ 4000 fluorescence plate reader and the instrument set to read from the top of the plate. The parameters for the plate reader are as follows: excitation filter settings at 485±10 nm; emission filter settings at 530±12.5 nm, and PMT gain set to 50. The samples are then read.

Example 3

Dry Down Plate Preparation

Some or all of the reagents necessary for the disclosed methods can be dried down for convenient storage and ease of use. For example, reactions can be set up as master mixes containing 40 mM Potassium acetate, 20 mM MgCl$_2$, 50 μM dNTPs (dATP, dCTP, dGTP, dTTP), 1 unit/reaction AMPLITAQ GOLD™ polymerase, a sugar as described below, and 8 μM reporter (e.g., labeled diGTP). The Master Mix can then be aliquoted into the wells of 96 well microtiter plates and dried in a SPEEDVAC™ (Savant Instruments, Holbrook, N.Y.) for 45-50 minutes (no heat). After desiccation, plates can be covered with MICROSEAL A™ film (MJ Reasearch, Waltham, Mass.) placed in a vacuum bag with 1 DESIPAK™ (Trocken, Germany), and the bag can be filled with argon and sealed with a FOOD SAVER™ (Tilia, San Franscisco, Calif.). Various sugars (Mannose, Raffinose, Sucrose, and Trehalose (Sigma, St. Louis, Mo.)) at various concentrations (1%, 2%, 5%, and 10% by weight) can be used.

Reaction mixes can be reconstituted in water containing nucleic acid target, first primer, second primer, and optionally reporter. The reaction mixes can then be subjected to PCR In this way, the dried down reagents can be readily reconstituted and successfully used in PCR assays. Such lyophilized reagents can be stored at room temperature for extended periods of time. Some or all of the reagents can be dried down. Some or all of the lyophilized reagents necessary for a given method of the disclosed methods can be stored in wells of microtiter plates for later use after reconstitution.

Example 4

Assay Including PCR Incorporation of Non-Natural Base

The labeled nucleotide triphosphate is incorporated into the elongating first primer during PCR extension. The label on the labeled nucleotide triphosphate is capable of quenching the label on the second primer. Alternatively fluorescence energy transfer (FRET) induction can be observed between the label of the second primer (donor dye) and the label of the reporter (acceptor dye). Detection of PCR product can be observed by exciting the donor dye and reading the emission of the incorporated acceptor dye.

Example 5

Detection of Neisseria

It has been discovered that various DNA extracts from bacteria, viruses, and other gene sequences of clinical interest can be reliably detected using PCR analysis of DNA extracted from liquid cytology medias (LCMs) including ThinPrep® and SurePath®. Commercially available assays and other laboratory developed assays exist for such applications. However, utilization of the disclosed methods offers opportunities for improved sensitivity and specificity for detecting specific target sequences of interest, as well as the ability to simultaneously evaluate multiple targets through multiplexed PCR amplification of DNA extracted from LCMs.

We have used the present methods to design an assay for the detection of Neisseria gonnorrhea and differentiation of such from other non-gonococcal cross-reactive species of Neisseria (N. subflava, N. perflava and N. cinerea) which have only minor genomic differences, and may be present in cervical cell specimens collected in liquid cytology medias. Sequence information utilized to generate PCR primers were found in the Entrez Nucleotides database, (which is available at the National Center for Biotechnology Information Website) and the Ribosomal Database Project, (which database is made available online by Michigan State University). The disclosed methods employ a multiplex system with an unlabeled conserved forward primer common to the aforementioned species of Neisseria, and a pair of fluorescently labeled discerning reverse primers, which differentiate N. gonorrhoeae from the non-gonococcal Neisseria species as a group. The primers are designed to amplify 99 bp and 98 bp fragments of the 16S ribosomal DNA gene, respectively. This method has particular significance for verification of N. gonorrhoeae in clinical specimens determined to be positive by other commercially available assays such as the Roche COBAS Amplicor, which may generate false positive results due to the cross-reactivity of the PCR primers used by this assay.

For the purposes of defining sensitivity and specificity of the assay, control organisms were purchased from American Type Culture Collection including N. gonorrohoeae Item No. 21825; N. subflava Item No. 19243; N. perflava Item No. 10555; N. cinerea Item No. 14685; N. mucosa Item No. 19693; N. lactima Item No. 23970; N. polysaccharea Item No. 43768; N. flavescens Item No. 13115; N. dentrificans Item No. 14686; N. meningitides 6250; and N. sicca Item No. 29193.

Purified culture of the above were quantified using flow cytometry to establish organism quantification. Dilutions of these organism stocks were utilized to create validation samples used to establish the performance characteristics of the RTx N. gonorrohoeae confirmatory assay.

Analysis of COBAS Amplicor Positive Negative and Indeterminate Specimens. Specimens collected in liquid cytology medias that were submitted for routine Neisseria gonorrhea analysis which tested positive by the Roche COBAS Amplicor assay were included in this study. Two hundred microliters of residual crude DNA extract was subjected to column-purification and eluted in 50 µL of PCR-grade water. Five microliters of the resulting DNA extract was utilized in a 20 µL multiplex real-time PCR reaction performed on the Roche LightCycler employing MultiCode®-RTx technology (Eragen Biosciences, Inc., Madison, Wis.). An unlabeled forward consensus PCR primer was designed to hybridize to each of the four Neisseria species targeted in this assay. Two labeled reverse genotyping primers are then utilized to specifically detect and discriminate between the presence of N. gonorrhea from non-gonococcal Neisseria species N. cinerea, N. subflava N. perflava, N. mucosa, N. lactima, N. polysaccharea, N. flavescens, N. dentrificans, N. meningitides, and N. sicca. Results are obtained in two-color format using HEX and FAM dyes and detected on F1 and F2 channels on a LightCycler® instrument.

MultiCode-RTx NG Confirmatory Assay Description. Initial assay design was implemented to detect and discern N. gonorrhea from 3 commonly reported non-gonococcal species N. subflava, N. cinerea, and N. perflava. The assay utilizes 3 primers as follows: 500 nM of an unlabeled forward consensus PCR primer was designed to hybridize to each of the four Neisseria species targeted. The first of two reverse genotyping primers, each at a concentration of 200 nM, is labeled with FAM and is utilized to specifically detect the presence of N. gonorrhoeae. The second genotyping assay is labeled with HEX and is utilized to detect the presence of any of the three other non-gonococcal Neisseria species (N. cinerea, N. subflava and N. perflava) which have been observed to cross react with the PCR primers used by in the Roche COBAS Amplicor assay (unpublished data). This assay utilizes the process of fluorescent resonance energy transfer (FRET) to quench the fluorescent signals from the genotyping primers as amplification occurs. Results are obtained in two-color format (color-compensated to minimize channel-to-channel "bleed-through") and confirmed via specific post-amplification melting temperature profiles. LightCycler® instrument amplification and melting data may be analyzed using suitable software. Samples are considered to be positive for the presence of N. gonorrhoeae or one or more of the cross-reacting Neisseria species based on cycle threshold ($C_T$) and melting temperature ($T_m$) for the specific, differentially-labeled primer sets.

The RTx N. gonorrhea assay utilized three primer pairs specific to the 16S ribosomal subunit gene:

```
SEQ ID NO: 1, FAM-(iC)GTCCCAGGTACCGTCATCG;

SEQ ID NO: 2, HEX-(iC)CAGGTCAGGTACCGTCATCA;

SEQ ID NO: 3, GCCATGCCGCGTGTCT
```

The real-time PCR reactions were assembled as follows:

| PCR Master Mix | Volume (µl) |
|---|---|
| PCR-grade H2O (Vial 10, colorless cap) | 1.5 |
| EraGen Isolution (2X) | 10 |
| MultiPlex Primer Mix (Primer Mix) | 3 |
| Titanium Taq | 0.5 |

Mix, add 15 µL to each capillary.
Add 5 µL of DNA from CT/NG Clean-up Procedure
PCR was performed and the reactions were monitored using a LightCycler® instrument under the following conditions:
94 C-2 min
(1 cycle)
94 C-10 sec
55 C-5 sec
(1 cycle)
72 C-20 sec—single acquisition
94 C-10 sec
64 C-10 sec
(54 cycles)
72 C-20 sec—single acquisition
60 C-30 sec
95 C (0.4 C/sec ramp w/step acquisition)—(Melt)
40 C-30 sec—(Cool)

Comparative assays were performed including an assay published by Tabrizi et al. which detects the cppB gene ("cppB assay"). See Tabrizi, S. N. et al. "Evaluation of real time Polymerase chain reaction assays for confirmation of Neisseria gonorrhoeae in clinical samples tested positive in the Roche Cobas Amplicor assay." SEX TRANSM. INFECT. 80: 68-71, 2004. In addition, a second comparative method for real-time PCR detection of N. gonorrhea, using a real-time PCR hyb probe for the 16S gene was utilized ("16S hyb probe assay").

Neisseria species were sequenced to confirm species type using the following primers in a PCR sequencing reaction:

```
FWD - CACTGGGACTGAGACACGGC;    (SEQ ID NO:8)

REV - CGTTAATCGGAATTACTGGGCGT  (SEQ ID NO:9)
```

Initial determinations of the lower limit of detection for N. gonorrhea, N. subflava, N. perflava and N. cinerea. Following quantification of these organisms using flow cytometry, 5-40 copies of each were diluted into PreservCyt media and Neisseria species were detected using the RTx real-time PCR assay. N. gonorrhea was detected in all reactions ranging from 5-40 copies per reaction as indicated by a signal in channel F1. The RTx assay showed positive findings for all non-gonococcal Neisseria samples containing 5-40 copies of either N. subflava, N. perflava, or N. cinerea. These studies indicated that the LLD of this assay was as low as 5 copies per reaction, and additional studies at 5 and 10 copies per reaction were performed. The N. gonorrhea specific primers are labeled with FAM and are detected on channel F1. It is noted that signal also appears in channel F2 when N. gonorrhea is present, but in the presence of non-gonococcal Neisseria species, the HEX signal is not detected in channel F1. This "bleed through" or spectral overlap seen with the FAM label is a consequence of the Light-Cycler® instrument, and can be somewhat overcome by color compensation programs. However, this instrument limitation does not affect the ability to discern N. gonorrhea from non-gonococcal Neisseria species as non-gonococcal Neisserias show a signal for the F2 channel only.

Results were obtained for the RTx real-time PCR detection of N. gonorrhea at 5 and 10 copies per PCR reaction. These concentrations were evaluated using 5 replicates at each concentration in PreservCyt, SurePath and M4 medias. The average $T_m$ at 10 copies per PCR reaction was found to be 85.4±0.2° C., 84.8.0±0.3° C., and 85.1±0.1° C. for PreservCyt, SurePath, and M4 medias respectively, while the $C_T$s were found to be 33.7±0.2 (PreservCyt), 33.6±0.3 (SurePath), and 35.6±0.5 (M4).

Similarly, at 5 copies per PCR reaction, the $T_m$ were 85.0±0.3° C., 84.7.0±0.2° C., and 84.6±0.4° C. for PreservCyt, SurePath, and M4 medias respectively, while the $C_T$s were found to be 35.3±0.2 (PreservCyt), 34.5±0.5 (SurePath), and 37.9±0.4 (M4), at this concentration in each of the three media types.

In order to demonstrate that the N. subflava, N. perflava, and N. cinerea non-gonococcal Neisseria species could be detected at the same LLD, RTx PCR studies were performed at 5 and 10 copies per PCR reaction for each of these species. Data was collected for 5 replicates at each concentration in PreservCyt media. All three species were detectable as indicated by an observed signal in channel F2 but not in channel F1. At 10 copies per reaction the mean $C_T$s were found to be 34.1±0.3 for N. cinerea, 34.3±0.4 for N. perflava, and 30.6± for N. subflava, while mean $T_m$s were 83.3±0.2° C., 83.2±0.2° C., and 84.1±0.4° C., respectively. At 5 copies per PCR reaction mean $C_T$s were found to be 34.1±0.4 for N. cinerea, 35.3±0.3 for N. perflava, and 32.4±0.4 for N. subflava while mean $T_m$s were 84.1±0.2° C., 83.0±0.4° C., and 83.5±0.4° C., respectively. These studies demonstrate that at the LLD of 5 copies per PCR reaction. N. gonorrhoeae and these 3 non-gonococcal species, all can be reliably detected at each of these concentrations with comparable efficiencies.

Detection of N. gonorrhoeae copy number in a mixed Neisseria cross reactor background. Studies to determine the performance of the RTx real time PCR assay under conditions where N. gonorrhea was present along with the N. subflava, N. perflava and N. cinerea cross reactive species (i.e., "cross-reactors") were performed.

In order to prepare a non-gonococcal Neisseria background for these studies, a mixture of organisms containing equal numbers of N. cinerea, N. perflava, and N. subflava was created following quantitation by flow cytometry.

Initially, the RTx real-time PCR assay was evaluated for test samples containing equivalent copy numbers of N. gonorrhea and cross-reactors at 5-800 copies of each per reaction in PreservCyt, SurePath, and M4 medias. Therefore, an "800 copy" sample contained 800 copies of N. gonorrhoeae and 800 copies of the non-gonococcal Neisseria mix which was prepared as described above. Signals were observed in both the channel F1 and channel F2. The $C_T$s for those reactions containing 800 copies per reaction of N. gonorrhea ranged from 27.0-27.9 for all 3 media types, and 800 copies of the non-gonococcal species ranged from 25.0-25.5. The $T_m$s ranged from 83.1° C. to 83.9° C. for N. gonorrhoeae specimens at this concentration, while the non-gonococcal $T_m$s ranged from 82.7-83.5° C. Those specimens containing 5 copies per PCR reaction of each of N. gonorrhoeae and non-gonococcal Neisseria demonstrated N. gonorrhea $C_T$s ranging form 34.1-35.2 while $C_T$s for the non-gonococcal species ranged from 31.9-32.4. The $T_m$s for N. gonorrhea ranged from 84.2-84.8° C. at 5 copies per PCR reaction, while non-gonococcal $T_m$s were found to be 82.7-83.5° C. when all 3 media types were compared.

The lower $C_T$s observed for the specimens with higher concentrations of *N. gonorrohoeae* and non-gonococcal *Neisseria* species is not surprising, as earlier detection of signal would be expected compared to those samples containing 5 copies of each *N. gonorrhea* and cross reactors. These data support the LLD of 5 copies per reaction, as positive results were noted for the presence of both *N. gonorrohoeae* and cross-reactors as indicated by HEX and FAM signals.

The RTx real-time PCR assay was then evaluated for eight replicates of 2 different low concentrations of *N. gonorrhea* in a highly concentrated background of non-gonococcal *Neisseria*. *N. gonorrhea* was diluted against a background of the non-gonococcal *Neisseria* (prepared as described previously) to concentrations of 2.5%, and 1.25%. Following analysis of eight replicates at each of these concentrations, it was demonstrated (as indicated by observed signals in channel F1 and channel F2) that *N. gonorrohoeae* could be reliably detected at a lower limit concentration of 1.25% in a background of non-gonococcal *Neisseria* with $C_T$s ranging from 36.2-38.3 for *Neisseria gonorrhea*, and 35.2-36.8 for non-gonococcal *Neisseria* at 1.25%. At 2.5% the $C_T$s for *N. gonorrhea* detection ranged from 25.1-26.0, and non-gonococcal *Neisseria* $C_T$s were 25.2-26.0. $T_m$s ranged from 83.8-84.1° C. (*N. gonorrohoeae*) and 82.3-82.9° C. (non-gonococcal *Neisseria*) at 1.25% *N. gonorrohoeae* concentrations and 83.8-84.2° C. (*N. gonorrohoeae*) and 82.3-82.9° C. (non-gonococcal *Neisseria*) at 2.5% *N. gonorrohoeae* concentrations. These data indicate that at 1.25 and 2.5% concentrations of *N. gonorrhea* in a background of *N. subflava*, *N. perflava*, and *N. cinera* the mean $C_T$s for *N. gonorrohoeae* were 35.7 and 37.1, respectively. The mean $T_m$s were 84.0° C. for both 1.25 and 2.5% concentrations of *N. gonorrohoeae*, while the $T_m$s for non-gonococcal *Neisseria* were 82.6° C. for both 1.25 and 2.5% *N. gonorrhea* concentrations as well.

In order to assess the RTx assay using actual clinical specimens, a total of 135 specimens collected in both PreservCyt and SurePath medias and previously analyzed using COBAS Amplicor were evaluated for the presence of *N. gonorrhea* using the RTx assay, 16S cppB assay, and 16S hyb probe assay. The results were then compared. See Table 2.

TABLE 2

Results for Samples 1-135

| Sample Number | Roche COBAS Amplicor Results | | | | NG 16S Hyb Probe | Optimized EraGen Primer Set | |
|---|---|---|---|---|---|---|---|
| | Initial OD | Repeat #1 OD | Repeat #2 OD | Reported Result | Conf. Assay Result | EraGen NG | Cross-Reactors |
| 1 | OUT | — | — | Pos | Pos | Pos | Pos |
| 2 | 3.699 | — | — | Pos | Pos | Pos | Pos |
| 3 | 3.695 | — | — | Pos | Pos | Pos | Pos |
| 4 | OUT | — | — | Pos | Pos | Pos | Not Detected |
| 5 | OUT | — | — | Pos | Not Detected | Not Detected | Not Detected |
| 6 | 3.350 | — | — | Pos | Not Detected | Not Detected | Pos |
| 7 | 3.525 | — | — | Pos | Not Detected | Not Detected | Pos |
| 8 | 2.534 | 3.155 | 3.699 | Pos | Not Detected | Not Detected | Not Detected |
| 9 | 3.619 | — | — | Pos | Not Detected | Not Detected | Pos |
| 10 | OUT | — | — | Pos | Not Detected | Not Detected | Pos |
| 11 | 3.919 | — | — | Pos | Not Detected | Not Detected | Pos |
| 12 | OUT | — | — | Pos | Pos | Pos | Not Detected |
| 13 | 3.745 | — | — | Pos | Not Detected | Not Detected | Pos |
| 14 | 2.124 | 2.415 | 2.165 | GZ Pos | Not Detected | Not Detected | Pos |
| 15 | 2.769 | 2.769 | 2.486 | GZ Pos | Not Detected | Not Detected | Pos |
| 16 | 2.380 | 2.876 | 2.966 | GZ Pos | Not Detected | Not Detected | Pos |
| 17 | OUT | — | — | Pos | Not Detected | Not Detected | Pos |
| 18 | OUT | — | — | Pos | Pos | Pos | Not Detected |
| 19 | 3.862 | OUT | — | Pos | Not Detected | Not Detected | Pos |
| 20 | OUT | 3.872 | — | Pos | Pos | Pos | Not Detected |
| 21 | 3.690 | 3.868 | — | Pos | Not Detected | Not Detected | Pos |
| 22 | OUT | OUT | — | Pos | Not Detected | Not Detected | Pos |
| 23 | OUT | OUT | — | Pos | Not Detected | Not Detected | Pos |

TABLE 2-continued

Results for Samples 1-135

| | Roche COBAS Amplicor Results | | | | NG 16S Hyb Probe | Optimized EraGen Primer Set | |
|---|---|---|---|---|---|---|---|
| Sample Number | Initial OD | Repeat #1 OD | Repeat #2 OD | Reported Result | Conf. Assay Result | EraGen NG | Cross-Reactors |
| 24 | 3.219 | 3.868 | 3.868 | GZ Pos | Not Detected | Not Detected | Pos |
| 25 | 2.604 | 3.567 | OUT | GZ Pos | Not Detected | Not Detected | Pos |
| 26 | 2.564 | 2.942 | 2.787 | GZ Pos | Not Detected | Not Detected | Pos |
| 27 | OUT | 2.515 | — | Pos | Not Detected | Not Detected | Pos |
| 28 | 3.587 | — | — | Pos | Pos | Pos | Not Detected |
| 29 | 3.711 | — | — | Pos | Not Detected | Not Detected | Pos |
| 30 | OUT | — | — | Pos | Not Detected | Not Detected | Pos |
| 31 | 3.702 | — | — | Pos | Not Detected | Not Detected | Pos |
| 32 | OUT | — | — | Pos | Not Detected | Not Detected | Pos |
| 33 | OUT | — | — | Pos | Not Detected | Not Detected | Pos |
| 34 | OUT | — | — | Pos | Not Detected | Not Detected | Pos |
| 35 | OUT | — | — | Pos | Pos | Pos | Not Detected |
| 36 | 3.703 | — | — | Pos | Not Detected | Not Detected | Pos |
| 37 | OUT | — | — | Pos | Pos | Pos | Not Detected |
| 38 | 3.534 | — | — | Pos | Not Detected | Not Detected | Pos |
| 39 | OUT | — | — | Pos | Pos | Pos | Not Detected |
| 40 | 3.585 | — | — | Pos | Not Detected | Not Detected | Pos |
| 41 | OUT | — | — | Pos | Not Detected | Not Detected | Pos |
| 42 | 2.675 | 3.574 | OUT | GZ Pos | Not Detected | Not Detected | Pos |
| 43 | OUT | OUT | — | Pos | Not Detected | Not Detected | Pos |
| 44 | OUT | OUT | — | Pos | Pos | Pos | Not Detected |
| 45 | OUT | 3.875 | — | Pos | Not Detected | Not Detected | Pos |
| 46 | OUT | OUT | — | Pos | Not Detected | Not Detected | Pos |
| 47 | OUT | OUT | — | Pos | Not Detected | Not Detected | Pos |
| 48 | OUT | OUT | — | Pos | Not Detected | Not Detected | Pos |
| 49 | 2.174 | 2.070 | 2.160 | GZ Pos | Not Detected | Not Detected | Not Detected |
| 50 | OUT | OUT | — | Pos | Pos | Pos | Pos |
| 51 | OUT | 2.676 | — | Pos | Not Detected | Not Detected | Pos |
| 52 | 3.576 | 3.773 | — | Pos | Not Detected | Not Detected | Pos |
| 53 | OUT | OUT | — | Pos | Not Detected | Not Detected | Pos |
| 54 | 1.876 | 2.118 | 2.041 | GZ Pos | Not Detected | Not Detected | Pos |
| 55 | OUT | — | — | Pos | Not Detected | Not Detected | Pos |
| 56 | OUT | — | — | Pos | Pos | Pos | Not Detected |
| 57 | 2.243 | 2.290 | 2.023 | GZ Pos | Not Detected | Not Detected | Pos |
| 58 | 3.891 | — | — | Pos | Not Detected | Not Detected | Pos |

TABLE 2-continued

Results for Samples 1-135

| | Roche COBAS Amplicor Results | | | | NG 16S Hyb Probe | Optimized EraGen Primer Set | |
|---|---|---|---|---|---|---|---|
| Sample Number | Initial OD | Repeat #1 OD | Repeat #2 OD | Reported Result | Conf. Assay Result | EraGen NG | Cross-Reactors |
| 59 | 3.220 | OUT | 3.876 | GZ Pos | Not Detected | Not Detected | Pos |
| 60 | 3.332 | — | — | Pos | Pos | Pos | Not Detected |
| 61 | OUT | OUT | — | Pos | Not Detected | Not Detected | Pos |
| 62 | 2.751 | 3.397 | 3.397 | GZ Pos | Not Detected | Not Detected | Pos |
| 63 | OUT | OUT | — | Pos | Not Detected | Not Detected | Pos |
| 64 | OUT | OUT | — | Pos | Not Detected | Not Detected | Pos |
| 65 | 3.317 | 3.862 | — | Pos | Not Detected | Not Detected | Pos |
| 66 | 3.773 | 3.597 | — | Pos | Pos | Pos | Not Detected |
| 67 | OUT | 3.698 | — | Pos | Pos | Pos | Not Detected |
| 68 | 2.044 | — | — | GZ Pos | Not Detected | Not Detected | Pos |
| 69 | OUT | OUT | — | Pos | Not Detected | Not Detected | Pos |
| 70 | 3.598 | OUT | — | Pos | Pos | Pos | Not Detected |
| 71 | 1.803 | 2.300 | 2.000 | GZ Pos | Not Detected | Not Detected | Pos |
| 72 | OUT | OUT | — | Pos | Pos | Pos | Not Detected |
| 73 | 3.582 | — | — | Pos | Not Detected | Not Detected | Pos |
| 74 | OUT | — | — | Pos | Pos | Pos | Not Detected |
| 75 | 2.263 | 3.013 | 2.623 | GZ Pos | Not Detected | Not Detected | Pos |
| 76 | 3.999 | — | — | Pos | Not Detected | Not Detected | Pos |
| 77 | OUT | — | — | Pos | Not Detected | Not Detected | Pos |
| 78 | OUT | — | — | Pos | Pos | Pos | Not Detected |
| 79 | 2.484 | 2.762 | 2.613 | GZ Pos | Not Detected | Not Detected | Not Detected |
| 80 | 3.895 | — | — | Pos | Pos | Pos | Not Detected |
| 81 | 1.836 | 2.287 | 3.207 | GZ Pos | Not Detected | Not Detected | Not Detected |
| 82 | 3.396 | 2.919 | — | Pos | Not Detected | Not Detected | Pos |
| 83 | OUT | OUT | — | Pos | Pos | Pos | Not Detected |
| 84 | 3.596 | OUT | — | Pos | Pos | Pos | Not Detected |
| 85 | 3.586 | 3.690 | — | Pos | Not Detected | Not Detected | Pos |
| 86 | OUT | — | — | Pos | Not Detected | Not Detected | Not Detected |
| 87 | OUT | — | — | Pos | Pos | Pos | Not Detected |
| 88 | OUT | — | — | Pos | Pos | Pos | Pos |
| 89 | OUT | — | — | Pos | Not Detected | Not Detected | Pos |
| 90 | 2.921 | 2.233 | 2.226 | GZ Pos | Not Detected | Not Detected | Pos |
| 91 | OUT | OUT | — | Pos | Not Detected | Not Detected | Pos |
| 92 | 2.267 | 2.922 | 3.068 | GZ Pos | Not Detected | Not Detected | Pos |
| 93 | 3.031 | 0.002 | 0.002 | GZ Pos | Not Detected | Not Detected | Pos |

TABLE 2-continued

Results for Samples 1-135

| Sample Number | Roche COBAS Amplicor Results | | | | NG 16S Hyb Probe | Optimized EraGen Primer Set | |
|---|---|---|---|---|---|---|---|
| | Initial OD | Repeat #1 OD | Repeat #2 OD | Reported Result | Conf. Assay Result | EraGen NG | Cross-Reactors |
| 94 | OUT | OUT | OUT | Pos | Not Detected | Not Detected | Pos |
| 95 | 3.865 | — | — | Pos | Pos | Pos | Pos |
| 96 | OUT | OUT | — | Pos | Not Detected | Pos | Not Detected |
| 97 | 3.056 | — | — | GZ Pos | Not Detected | Not Detected | Pos |
| 98 | 3.367 | OUT | — | Pos | Not Detected | Not Detected | Pos |
| 99 | OUT | OUT | — | Pos | Not Detected | Not Detected | Pos |
| 100 | 3.451 | — | — | Pos | Pos | Pos | Not Detected |
| 101 | 3.327 | — | — | Pos | Not Detected | Not Detected | Pos |
| 102 | 4.000 | — | — | Pos | Pos | Pos | Not Detected |
| 103 | 3.707 | — | — | Pos | Not Detected | Not Detected | Pos |
| 104 | 3.700 | — | — | Pos | Pos | Pos | Not Detected |
| 105 | OUT | — | — | Pos | Pos | Pos | Not Detected |
| 106 | OUT | — | — | Pos | Pos | Pos | Not Detected |
| 107 | OUT | — | — | Pos | Not Detected | Not Detected | Pos |
| 108 | 2.096 | 2.881 | 3.525 | GZ Pos | Not Detected | Not Detected | Pos |
| 109 | OUT | — | — | Pos | Not Detected | Not Detected | Pos |
| 110 | OUT | — | — | Pos | Not Detected | Not Detected | Pos |
| 111 | 2.850 | 3.016 | 3.104 | GZ Pos | Not Detected | Not Detected | Pos |
| 112 | 3.701 | — | — | Pos | Not Detected | Not Detected | Pos |
| 113 | 3.525 | — | — | Pos | Pos | Pos | Pos |
| 114 | OUT | — | — | Pos | Not Detected | Not Detected | Pos |
| 115 | OUT | — | — | Pos | Not Detected | Not Detected | Pos |
| 116 | OUT | — | — | Pos | Pos | Pos | Not Detected |
| 117 | 2.903 | 3.101 | 2.880 | GZ Pos | Not Detected | Not Detected | Pos |
| 118 | OUT | — | — | Pos | Pos | Pos | Not Detected |
| 119 | 3.688 | — | — | Pos | Not Detected | Not Detected | Pos |
| 120 | OUT | — | — | Pos | Pos | Pos | Not Detected |
| 121 | OUT | — | — | Pos | Not Detected | Pos | Not Detected |
| 122 | 1.714 | 2.339 | 2.204 | GZ Pos | Not Detected | Not Detected | Pos |
| 123 | 3.989 | — | — | Pos | Not Detected | Not Detected | Pos |
| 124 | 2.798 | 2.541 | 2.748 | GZ Pos | Not Detected | Not Detected | Pos |
| 125 | 3.228 | 2.748 | 3.401 | GZ Pos | Not Detected | Not Detected | Pos |
| 126 | OUT | — | — | Pos | Pos | Pos | Pos |
| 127 | OUT | — | — | Pos | Not Detected | Not Detected | Pos |
| 128 | OUT | — | — | Pos | Pos | Pos | Not Detected |
| 129 | 3.929 | — | — | Pos | Pos | Pos | Not Detected |

TABLE 2-continued

Results for Samples 1-135

| Sample Number | Roche COBAS Amplicor Results | | | NG 16S Hyb Probe | Optimized EraGen Primer Set | |
| --- | --- | --- | --- | --- | --- | --- |
| | Initial OD | Repeat #1 OD | Repeat #2 OD | Reported Result | Conf. Assay Result | EraGen NG | Cross-Reactors |
| 130 | 2.555 | 0.003 | 2.851 | GZ Pos | Not Detected | Not Detected | Pos |
| 131 | 3.754 | — | — | Pos | Pos | Pos | Not Detected |
| 132 | OUT | — | — | Pos | Pos | Pos | Pos |
| 133 | 3.918 | — | — | Pos | Pos | Pos | Not Detected |
| 134 | 4.000 | — | — | Pos | Pos | Pos | Not Detected |
| 135 | OUT | — | — | Pos | Not Detected | Pos | Pos |

Of 135 COBAS positive specimens, 46 (34.1%) were found to be *N. gonorrhea* positive using the RTx assay. Of the remaining specimens, 89 (64%) had a negative finding using RTx. Comparison of the RTx findings to results from the other 2 real-time PCR assays showed a 97.8% concordance with the 16S hyb probe assay (3 descrepant samples were RTx positive and hyb probe negative), and a 91.1% concordance with the cppB assay (7 samples which were RTx positive, cppB assay negative; and 5 samples which were RTx negative, and cppB assay positive). See Table 3.

TABLE 3

Confirmatory Assay Concordances

| | | MultiCode-RTx NG Confirmatory Assay | |
| --- | --- | --- | --- |
| | | Pos | Neg |
| 16S Hyb Probe Assay | Pos | 43 | 0 |
| | Neg | 3 | 89 |
| | | Overall Concordance - 97.8% | |
| cppB Beacon Assay | Pos | 39 | 5* |
| | Neg | 7** | 84 |
| | | Overall Concordance - 91.1% | |

Sequencing studies were undertaken to resolve discrepant sample results. Of the 3 specimens which were RTx positive and 16S hyb probe negative, sequencing results showed the presence of mixed bacteria, while a third specimen could not be sequenced due to exhaustion of the specimen. Neither specimen where mixed bacteria were identified contained *N. cinerea, N. perflava,* or *N. subflava* sequences or other non-gonococcal *Neisseria* sequences. The presence of *N. gonorrhea* in these specimens could not be ruled out and may be difficult to detect under the circumstances of mixed genomes. Of the 7 specimens which were RTx *N. gonorrhea* positive and cppB assay negative, 4/4 samples which were sequenced confirmed the presence of *N. gonorrhoeae* in these specimens. Of the 85 specimens which were RTx *N. gonorrhea* negative, no discordant results were obtained compared to findings observed following analysis with the 16S hyb probe assay, while 5 specimens were found to be RTx negative and cppB assay positive. Individual PCR analysis using individual primer pairs type-specific to *N. cinerea, N. subflava,* and *N. perflava* indicate that 4/5 were found to have positive findings for one or more of these 3 *Neisseria* non-gonococcal species, while the 5$^{th}$ specimen did not demonstrate the presence of any of these 3 non-gonococcal species with type specific PCR, but was found to be positive using the RTx assay non-gonococcal consensus primers. Sequencing of the 4 non-gonococcal type-specific PCR positive specimens indicated that 3/4 showed presence of mixed bacteria, while the 4$^{th}$ showed the presence *N. meningitis*. All 4 of these specimens were RTx assay positive using the non-gonococcal *Neisseria* consensus primers. The 5$^{th}$ specimen may contain other *Neisseria* species not identified by the individual *N. cinerea, N. subflava,* or *N. perflava* primer pairs.

Following flow cytometric quantitation of additional non-gonococcal *Neisseria* species *N. mucosa, N. lactima, N. polysaccharea, N. flavescens, N. dentrificans, N. meningitides,* and *N. sicca,* the MultiCode-RTx assay was performed as described above. A detectable signal was not observed for any of the organisms tested in the channel F1, with the exception of *N. dentrificans,* which showed a signal which was detected during late cycles of the assay (Cycles 49 and higher). This may indicate some cross-reactivity, as the data suggest that *N. gonorrhea,* is usually detected during earlier cycles. Samples which show this late pattern should be further evaluated as ongoing QA/QC for this assay.

It will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

In addition, where features or aspects of the invention are described in terms of Markush groups or other grouping of alternatives, those skilled in the art will recognize that the invention is also thereby described in terms of any individual member, any subgroup of members of the Markush group or other group, or the totality of members of the Markush group or other group.

Also, unless indicated to the contrary, where various numerical values are provided for embodiments, additional embodiments are described by taking any 2 different values as the endpoints of a range. Such ranges are also within the scope of the described invention.

What is claimed is:

1. A method for detecting *Neisseria* in a sample comprising:
   (a) reacting a mixture comprising:
      (i) nucleic acid isolated from the sample;
      (ii) at least a first specific primer capable of being used to amplify nucleic acid of *Neisseria gonorrhea*, wherein the sequence of the first primer consists of SEQ ID NO: 1;
      (iii) at least a second specific primer capable of being used to amplify nucleic acid of at least one non-gonococcal species of *Neisseria*, wherein the sequence of the second primer consists of SEQ ID NO: 2;
      wherein at least one of the first specific primer and the second specific primer comprise a first non-natural nucleotide base and a label;
      (iv) at least a universal primer capable of being used to amplify nucleic acid of *Neisseria gonorrhea* and nucleic acid of the at least one non-gonococcal species of *Neisseria*;
      (v) a second non-natural nucleotide base conjugated to a quencher;
   (b) performing an amplification reaction with the primers of step (a) to produce amplification products of nucleic acid of at least one of *Neisseria gonorrhea* and the at least one non-gonococcal species of *Neisseria*, if present, wherein the second non-natural nucleotide base is incorporated opposite the first non-natural nucleotide base; and
   (c) detecting the amplification products by observing a signal from the label, wherein the signal may be quenched upon incorporation of the second non-natural nucleotide base into the amplification products.

2. The method of claim 1, wherein the non-gonococcal species of *Neisseria* is selected from the group consisting of *Neisseria subflava*, *Neisseria cinerea*, *Neisseria perflava* and combinations thereof.

3. The method of claim 1, wherein the label comprises a fluorophore.

4. The method of claim 3, wherein the first specific primer comprises the first non-natural nucleotide base conjugated to a first fluorophore and the second specific primer includes another non-natural nucleotide base conjugated to a second fluorophore which is different than the first fluorophore.

5. The method of claim 1, wherein the first non-natural nucleotide base comprises iC or iG.

6. The method of claim 4, wherein the second non-natural nucleotide base is conjugated to a fluorescence quencher.

7. The method of claim 6, wherein the second non-natural nucleotide base is conjugated to a fluorescence quencher that is capable of quenching the first fluorophore and the second fluorophore.

8. The method of claim 3, wherein detecting comprises observing a change in fluorescence of the fluorophore.

9. The method of claim 8, wherein the change in fluorescence is a decrease in fluorescence.

10. The method of claim 1, wherein the amplified nucleic acid is detected during amplification.

11. The method of claim 1 wherein the amplified nucleic acid is detected after amplification.

12. The method of claim 1, wherein at least one of the first specific primer, the second specific primer, and the universal primer is capable of specifically hybridizing to 16S ribosomal nucleic acid of *Neisseria*.

13. The method of claim 12, wherein the first specific primer, the second specific primer, and the universal primer are capable of specifically hybridizing to 16S ribosomal nucleic acid of *Neisseria*.

14. The method of claim 1, wherein the universal primer comprises SEQ ID NO: 3.

15. The method of claim 1, wherein the reaction mixture further comprises amplification reagents.

16. The method of claim 1, wherein the second non-natural nucleotide base is complementary to the first non-natural nucleotide base.

* * * * *